(12) United States Patent
Zhang et al.

(10) Patent No.: US 6,436,915 B1
(45) Date of Patent: Aug. 20, 2002

(54) PYRAZOLE COMPOUNDS

(75) Inventors: Zaihui Zhang, Richmond; Timothy Scott Daynard, Vancouver; Shisen Wang, Coquitlam; Mikhail Chafeev, Vancouver, all of (CA)

(73) Assignee: Kinetek Pharmaceuticals, Inc., Vancouver (CA)

( * ) Notice: Subject to any disclaimer, the term of this patent is extended or adjusted under 35 U.S.C. 154(b) by 0 days.

(21) Appl. No.: 09/747,563

(22) Filed: Dec. 22, 2000

Related U.S. Application Data

(63) Continuation-in-part of application No. 09/544,908, filed on Apr. 7, 2000, now Pat. No. 6,214,813.

(51) Int. Cl.$^7$ ................... A61K 31/415; A61K 31/655
(52) U.S. Cl. .................. 514/150; 514/151; 514/404; 514/406
(58) Field of Search ................. 514/150, 151, 514/404, 406

(56) References Cited

FOREIGN PATENT DOCUMENTS

| WO | WO 01/56557 A2 | 9/2001 |
|----|----------------|--------|
| WO | WO 01/56993 A2 | 9/2001 |
| WO | WO 01/57022 A2 | 9/2001 |

OTHER PUBLICATIONS

Delcommenne et al. (Sep. 1998), "Phosphoinositide–3–OH Kinase–Dependent Regulation of Glycogen Synthase Kinase 3 and Protein Kinase B/AKT by the Integrin–Linked Kinase," *Proc. Natl. Acad. Sci. USA,* vol. 95:11211–6.

Kandeel et al. (1985), "Activated Nitriles in Heterocyclic Synthesis: Reaction of Cyanogen Bromide with some Functionality Substituted Enamines, " *J. Chem. Sok. Perkin. Trans.,* pp. 1499–1501.

Dubenko et al., Chemical Abstracts, 69:18743, 1968.*

Kitaev et al., Chemical Abstracts, 82:66061, 1975.*

Studennikova et al., Chemical Abstracts, 105:191071, 1986.*

Database Ca 'Online! Chemical Abstracts Service, Columbus, Ohio, US; El–Shahat Kandeel, Zaghloul et al.: "Oxidative transformation of pyrazole into triazole. Novel synthesis of 4–cyano–2H–1, 2,3–triazole derivatives" retrieved from STN Database accession No. 108: 131679 XP002182981 see compounds with RN=99285–51–5; 113470–86–3; 113470–89–6 & J. Chem. Soc., Perkin Trans. 1 (1986), (8), 1379–81.

Database Ca 'Online! Chemical Abstracts Service, Columbus, Ohio, US; Elnagdi, Mohamed Hilmy et al.: "Reactions with cyclic amidines. III: Synthesis of some new fused pyrazole derivatives" retrieved from STN database accession No. 91:39437 XP002182982 compound with RN=70649–20–6 & Z. Naturforsch., B: Anorg. Chem., Org. Chem. (1979), 34B(2), 275–9.

Database Ca 'Online! Chemical Abstracts Service, Columbus, Ohio, US; Elnagdi, Mohamed H. et al.: "Reaction with the arylhydrazones of some.alpha.–cyano ketones" retrieved from STN Database accession No. 80:82349 XP002182984 see compound with RN=51337–57–6 & J. Prakt. Chem. (1973), 315(6), 1009–16.

Database Ca 'Online! Chemical Abstracts Service, Columbus, Ohio, US; Elnagdi, Mohamed H. et al.: "3,5–Pyrazolidinediones. IV. Addition of 4–arylazo–3,5–pyrazolidinediones to ethyl acrylate" retrieved from STN Database accession No. 79: 78677 XP002182985 compound with RN=42390–11–4 & Bull. Chem. Soc. Jap. (1973), 46(6), 1830–3.

Database Ca 'Online! Chemical Abstracts Service, Columbus, Ohio, US; Rafat Mahmound, Mohamed et al.: "Electronic spectral properties of some arylazoaminopyrazolones" retrieved from STN Database accession No. 101:130079 XP002182986 compounds with RN=3656–09–5; 4584–01–4; 19197–14–9 & Bull. Soc. Chim. Fr. (1984), (3–4, Pt. 2), 164–7.

Database Ca 'Online! Chemical Abstracts Service, Columbus, Ohio, US; Yuh–Wen, Ho: "Studies on the synthesis of new 3–'(3,5–diamino–1–substituted–pyrazol–4–yl) azo!thieno '2,3–b!pyridines" retrieved from STN Database accession No. 132:194356 XP002182987 compound with RN=259854–44–9 & J. Chin. Chem. Soc. (Taipei) (1999), 46(6), 955–962.

Database Ca 'Online! Chemical Abstracts Service, Columbus, Ohio, US; Sherif, Sherif M. et al.: "A convenient synthesis of polyfunctionally substituted benzo 'b! thiophen–2–ylpyrimidine, –pyrazole,–isoxazole and – pyridazine derivatives" retrieved from STN Database accession No. 124:146056 XP002182988 compound with RN=173540–19–7 & J. Chem. Res., Synop. (1995), (11), 434–5.

(List continued on next page.)

*Primary Examiner*—Fiona T. Powers
(74) *Attorney, Agent, or Firm*—Pamela J. Sherwood; Bozicevic, Field & Francis LLP

(57) ABSTRACT

Pharmaceutical compositions and compounds are provided. The compounds of the invention have anti-proliferative activity, and may promote apoptosis in cells lacking normal regulation of cell cycle and death. In one embodiment of the invention, formulations of the compounds in combination with a physiologically acceptable carrier are provided. The pharmaceutical formulations are useful in the treatment of hyperproliferative disorders, which disorders include tumor growth, lymphoproliferative diseases, angiogenesis. The compounds of the invention are substituted pyrazoles and pyrazolines.

26 Claims, 1 Drawing Sheet

OTHER PUBLICATIONS

Database Ca 'Online! Chemical Abstracts Service, Columbus, Ohio, US; Liu, Bo et al.: "Synthesis of some new benzothiazolylazopyrazoles and benzothiazolylazopyrimidines" retrieved from STN Database accession No. 121: 9222 XP002182989 compounds with RN=153471–54–6; 153471–57–9 & Youji Huaxue (1994), 14(2), 206–10.

Database Ca 'Online! Chemical Abstracts Service, Columbus, Ohio, US; Hassan, Alaa A. et al.: "Chemical interactions between aminopyrazoles and 2,3–dicyano–1,4–naphthoquinone" retrieved from STN Database accession No. 120:8545 XP002182990 compound with RN=151293–14–0 &Liebigs Ann. Chem. (1993), (6), 695–7.

Database Ca 'Online! Chemical Abstracts Service, Columbus, Ohio, US; Baig, Ghouse Unissa et al.: "Triazines and related products. Part 24. Synthesis of pyrazol–4–ylidenehydrazinoimidazoles by hydrazinolysis of imidazo '5, 1–c! "1,2,4!triazines and 2–arylazoimidazoles by diazonium coupling reactions" retrieved from STN Database accession No. 97:162888 XP002182991 83296–75–7 & J. Chem. Soc., Perkin Trans. 1 (1982), (8), 1811–19.

* cited by examiner

PYRAZOLE COMPOUNDS

This application in a continuation-in-part of U.S. patent application Ser. No. 09/544,908, filed Apr. 7, 2000, now U.S. Pat. No. 6,214,813.

BACKGROUND OF THE INVENTION

It has become increasingly clear in recent years that cell death is as important to the health of a multicellular organism as cell division: where proliferation exists, so must a means of regulating its cellular progeny. By repeated cell division and differentiation throughout development or tissue repair, surplus or even harmful cells are generated, and they must be removed or killed. In adults, senescent cells are removed and replaced by newly generated cells to maintain homeostasis.

The delicate interplay between growth and cell death in an organism is mirrored in the complex molecular balance that determines whether an individual cell undergoes division; arrests in the cell cycle; or commits to programmed cell death. Signal transduction is the term describing the process of conversion of extracellular signals, such as hormones, growth factors, neurotransmitters, cytokines, and others, to a specific intracellular response such as gene expression, cell division, or apoptosis. This process begins at the cell membrane where an external stimulus initiates a cascade of enzymatic reactions inside the cell that typically include phosphorylation of proteins as mediators of downstream processes which most often end in an event in the cell nucleus. The checks and balances of these signal transduction pathways can be thought of as overlapping networks of interacting molecules that control "go-no go" control points. Since almost all known diseases exhibit dysfunctional aspects in these networks, there has been a great deal of enthusiasm for research that provides targets and therapeutic agents based on signal transduction components linked to disease.

Dysregulation of cell proliferation, or a lack of appropriate cell death, has wide ranging clinical implications. A number of diseases associated with such dysregulation involve hyperproliferation, inflammation, tissue remodelling and repair. Familiar indications in this category include cancers, restenosis, neointimal hyperplasia, angiogenesis, endometriosis, lymphoproliferative disorders, graft-rejection, polyposis, loss of neural function in the case of tissue remodelling, and the like. Such cells may lose the normal regulatory control of cell division, and may also fail to undergo appropriate cell death.

In one example, epithelial cells, endothelial cells, muscle cells, and others undergo apoptosis when they lose contact with extracellular matrix, or bind through an inappropriate integrin. This phenomenon, which has been termed "anoikis" (the Greek word for "homelessness"), prevents shed epithelial cells from colonizing elsewhere, thus protecting against neoplasia, endometriosis, and the like. It is also an important mechanism in the initial cavitation step of embryonic development, in mammary gland involution, and has been exploited to prevent tumor angiogenesis. Epithelial cells may become resistant to anoikis through overactivation of integrin signaling. Anoikis resistance can also arise from the loss of apoptotic signaling, for example, by overexpression of Bcl-2 or inhibition of caspase activity.

An aspect of hyperproliferation that is often linked to tumor growth is angiogenesis. The growth of new blood vessels is essential for the later stages of solid tumor growth. Angiogenesis is caused by the migration and proliferation of the endothelial cells that form blood vessels.

In another example, a major group of systemic autoimmune diseases is associated with abnormal lymphoproliferation, as a result of defects in the termination of lymphocyte activation and growth. Often such diseases are associated with inflammation, for example with rheumatoid arthritis, insulin dependent diabetes mellitus, multiple sclerosis, systemic lupus erythematosus, and the like. Recent progress has been made in understanding the causes and consequences of these abnormalities. At the molecular level, multiple defects may occur, which result in a failure to set up a functional apoptotic machinery.

The development of compounds that inhibit hyperproliferative diseases, particularly where undesirable cells are selectively targeted, is of great medical and commercial interest.

Relevant Literature:

The regulation of integrin linked kinase by phosphatidylinositol (3,4,5) trisphosphate is described by Delcommenne et al. (1998) *Proc Natl Acad Sci* 95:11211–6. Activated nitriles in heterocyclic synthesis are discussed in Kandeel et al. (1985) *J. Chem. Soc. Perkin. Trans* 1499.

SUMMARY OF THE INVENTION

Pharmaceutical compositions and compounds are provided. The compounds of the invention are substituted pyrazoles and pyrazolines. In one embodiment of the invention, formulations of the compounds in combination with a physiologically acceptable carrier are provided. The pharmaceutical formulations are useful in the treatment of disorders associated with hyperproliferation and tissue remodelling or repair. The compounds are also active in the inhibition of specific protein kinases.

DETAILED DESCRIPTION OF EMBODIMENTS OF THE INVENTION

Figure 1:
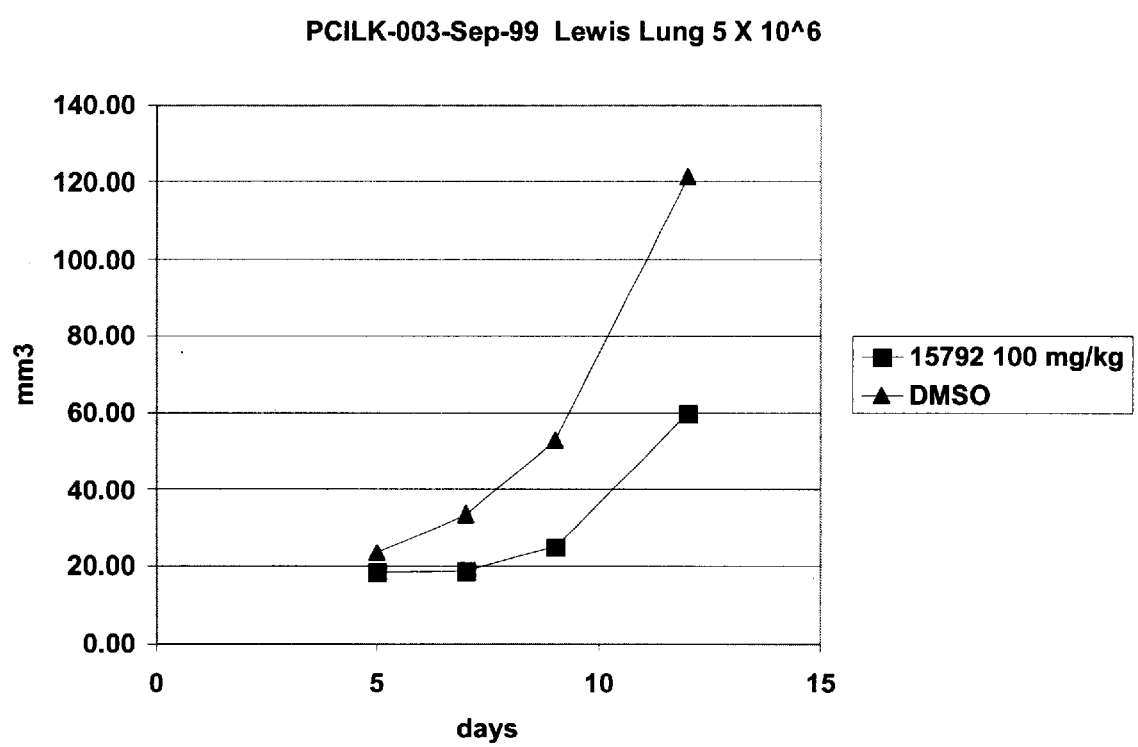
FIG. 1 is a graph illustrating the anti-tumor activity of KP-15792 in a murine model using Lewis Lung Carcinoma cells.

The present invention provides novel compounds, compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

DEFINITION OF TERMS

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

"Alkyl" is a monovalent, saturated or unsaturated, straight, branched or cyclic, aliphatic (i.e., not aromatic) hydrocarbon group. In various embodiments, the alkyl group has 1–20 carbon atoms, i.e., is a C1–C20 (or $C_1$–$C_{20}$) group, or is a C1–C18 group, a C1–C12 group, a C1–C6 group, or a C1–C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH=$CH_2$ (ethenyl) and —C≡CH (ethynyl)) and $C_3$alkyl (i.e., —$CH_2CH_2CH_3$ (n-propyl), —$CH(CH_3)_2$ (i-propyl), —CH=CH—$CH_3$ (1-propenyl), —C≡C—$CH_3$ (1-propynyl), —$CH_2$—CH=$CH_2$ (2-propenyl), —$CH_2$—C≡CH (2-propynyl), —$C(CH_3)$=$CH_2$ (1-methylethenyl), and —$CH(CH_2)_2$ (cyclopropyl)).

"Ar" indicates a carbocyclic aryl group selected from phenyl, substituted phenyl, naphthyl, and substituted naphthyl. Suitable substituents on a phenyl or naphthyl ring include $C_1$–$C_6$alkyl, $C_1$–$C_6$alkoxy, carboxyl, carbonyl ($C_1$–$C_6$)alkoxy, halogen, hydroxyl, nitro, —$SO_3H$, and amino.

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group.

"Arylene" is a polyvalent, aromatic hydrocarbon, ring system. The ring system may be monocyclic or fused polycyclic (e.g., bicyclic, tricyclic, etc.). In various embodiments, the monocyclic arylene group is C5–C10, or C5–C7, or C5–C6, where these carbon numbers refer to the number of carbon atoms that form the ring system. A C6 ring system, i.e., a phenylene ring, is a preferred aryl group. In various embodiments, the polycyclic ring is a bicyclic arylene group, where preferred bicyclic arylene groups are C8–C12, or C9–C10. A naphthylene ring, which has 10 carbon atoms, is a preferred polycyclic aryl group. The arylene group may be divalent, i.e., it has two open sites that each bond to another group; or trivalent, i.e., it has three open sites that each bond to another group; or it may have more than three open sites.

"Carbocycle" refers to a ring formed exclusively from carbon, which may be saturated or unsaturated, including aromatic. The ring may be monocyclic (e.g., cyclohexyl, phenyl), bicyclic (e.g., norbomyl), polycyclic (e.g., adamantyl) or contain a fused ring system (e.g., decalinyl, naphthyl). In one embodiment, the ring is monocyclic and formed from 5, 6 or 7 carbons. In one embodiment, the ring is bicyclic and formed from 7, 8 or 9 carbons. In one embodiment, the ring is polycyclic and formed from 9, 10 or 11 carbons. In one embodiment, the ring includes a fused ring system and is formed from 8–12 carbons. Thus, in one embodiment, the carbocycle is formed from 5–12 ring carbons.

"Heteroalkyl" is an alkyl group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. As another example, trifluoromethyl is a heteroalkyl group wherein the three methyl groups of a t-butyl group are replaced by fluorine.

"Heteroalkylene" is an alkylene group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom, as explained elsewhere herein.

"Heteroaryl" is a monovalent aromatic ring system containing carbon and at least one heteroatom in the ring. The heteroaryl group may, in various embodiments, have one heteroatom, or 1–2 heteroatoms, or 1–3 heteroatoms, or 1–4 heteroatoms in the ring. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroarylene" is a polyvalent aromatic ring system containing carbon and at least one heteroatom in the ring. In other words, a heteroarylene group is a heteroaryl group that has more than one open site for bonding to other groups. The heteroarylene group may, in various embodiments, have one heteroatom, or 1–2 heteroatoms, or 1–3 heteroatoms, or 1–4 heteroatoms in the ring. Heteroarylene rings may be monocyclic or polycyclic, where the polycyclic ring may contained fused, spiro or bridged ring junctions. In one embodiment, the heteroaryl is selected from monocyclic and bicyclic. Monocyclic heteroarylene rings may contain from about 5 to about 10 member atoms (carbon and heteroatoms), preferably from 5–7, and most preferably from 5–6 member atoms in the ring. Bicyclic heteroarylene rings may contain from about 8–12 member atoms, or 9–10 member atoms in the ring.

"Heteroatom" is a halogen, nitrogen, oxygen, silicon or sulfur atom. Groups containing more than one heteroatom may contain different heteroatoms.

"Heterocycle" refers to a ring containing at least one carbon and at least one heteroatom. The ring may be monocyclic (e.g., morpholinyl, pyridyl), bicyclic (e.g., bicyclo[2.2.2]octyl with a nitrogen at one bridgehead position), polycyclic, or contain a fused ring system. In one embodiment, the ring is monocyclic and formed from 5, 6 or 7 atoms. In one embodiment, the ring is bicyclic and formed from 7, 8 or 9 atoms. In one embodiment, the ring is polycyclic and formed from 9, 10 or 11 atoms. In one embodiment, the ring includes a fused ring system and is formed from 8–12 atoms. Thus, in one embodiment the heterocycle is formed from 5–12 ring atoms. In one embodiment, the heteroatom is selected from oxygen, nitrogen and sulfur. In one embodiment, the heterocycle contains 1, 2 or 3 heteroatoms.

As used herein, and unless otherwise specified, the terms carbocyclic and heterocyclic encompass both substituted and unsubstituted carbocyclic and heterocyclic groups. In one embodiment, the substitution present on a carbocyclic or heterocyclic group is selected from alkyl, heteroalkyl, aryl, and heteroaryl, preferably alkyl and heteroalkyl. In one embodiment, the alkyl and heteroalkyl substitution present on a carbocyclic or heterocyclic group is selected from $C_1$–$C_6$alkyl, $C_1$–$C_6$alkoxy, halogen, nitro, hydroxyl, cyano, sulfonic acid (i.e., —$SO_3H$), carboxylic acid, carboxylate ester (i.e., —$CO_2R$ where R is, e.g., $C_1$–$C_{10}$alkyl), amino, alkylamino, dialkylamino, acyl (i.e., R—C(=O)—), and acylamino (i.e., R—C(=O)—NH— where R is, e.g., $C_1$–$C_{10}$alkyl). For example, and unless otherwise specified, the terms cyclohexyl and phenyl refer to both substituted and unsubstituted cyclohexyl and phenyl.

"Pharmaceutically acceptable salt" and "salts thereof" in the compounds of the present invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

COMPOUNDS

In one aspect the present invention provides compounds of formula (1), as set forth below.

In another aspect the present invention provides compositions comprising a compound of formula (1)

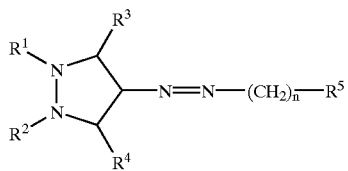

(1)

and stereoisomers, solvates, and pharmaceutically acceptable salts thereof, and a pharmaceutically acceptable carrier, diluent or excipient, where $R^1$ and $R^2$ are selected from direct bond, H, and alkyl;

$R^3$ and $R^4$ are selected from —$NH_2$, NHC(=O)$R^5$, and =O;

$R^5$ is selected from $R^6$, $R^7$, and $R^8$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; $R^8$ is selected from $(R^7)_k$-alkylene, $(R^7)_k$-heteroalkylene, $(R^7)_k$-arylene, and $(R^7)_k$-heteroarylene; and k is selected from 0, 1, 2, 3, 4 and 5; and n is selected from 0, 1, 2, 3, 4 or 5.

In another aspect, the present invention provides compounds of formula (1) and compositions comprising compounds of formula (1) as drawn above, wherein $R^1$ is selected from alkyl, aryl and heteroaryl, wherein each of alkyl, aryl and heteroaryl may be substituted with one or more groups selected from $C_1$–$C_{20}$alkyl, $C_6$–$C_{10}$aryl, heteroalkyl and heteroaryl; $R^2$ is selected from H and direct bond; $R^3$ and $R^4$ are selected from —$NH_2$ and NHC(=O)$R^5$; $R^5$ is selected from $R^6$, $R^7$, and $R^8$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; $R^8$ is selected from $(R^7)_k$-alkylene, $(R^7)_k$-heteroalkylene, $(R^7)_k$-arylene, and $(R^7)_k$-heteroarylene; and k is selected from 0, 1, 2, 3, 4 and 5; and n is selected from 0, 1, 2, 3, 4 or 5.

In various embodiments, $R^1$ is $C_1$–$C_{20}$alkyl; or $R^1$ is $C_1$–$C_6$alkyl and each of $R^3$ and $R^4$ are —$NH_2$; or $R^1$ is aryl; or $R^1$ is aryl selected from phenyl and naphthyl, the phenyl and napthyl substituted with at least one heteroalkyl selected from alkoxy, carboxy and halide; and/or each of $R^3$ and $R^4$ are —$NH_2$; and/or $R^5$ is selected from carbocyclic and heterocyclic groups, wherein the carbocyclic and heterocyclic groups may optionally contain 5–12 ring atoms. In other embodiments, wherein $R^5$ is a carbocyclic group selected from monocyclic and fused ring groups, or $R^5$ is a heterocyclic group containing from 1–3 nitrogens; or $R^5$ is selected from $R^6$ and $R^7$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; and k is selected from 0, 1, 2, 3, 4 and 5.

In another embodiment, $R^5$ is selected from 4-fluorophenyl, 3-ethylphenyl, 3-methoxyphenyl, 3-chlorophenyl, 3-fluorophenyl, 3-fluoro-4-methoxyphenyl, naphthalen-2-yl, 4-trifluoromethylphenyl, 3-phenoxyphenyl, biphenyl-2-yl, 2-bromophenyl, 3-bromophenyl, 4-bromophenyl, 4-phenoxyphenyl, 4-iodophenyl, 4-bromonaphthalen-1-yl, o-tolyl, 2,6-difluorophenyl, 3,4-difluorophenyl, benzo[1,3]dioxol-5-yl, 4-methylsulfanylphenyl, 2,3-dihydrobenzo[1,4]dioxin-6-yl, 3-chloro-4-methoxyphenyl, 3,4-dichlorophenyl, 3,5-dichlorophenyl, 2-isopropylphenyl, 3,4-dimethoxyphenyl, 3-trifluoromethylphenyl, 3-methoxy-5-trifluoromethylphenyl, 2-chlorophenyl, 3-iodophenyl, 9-ethyl-9H-carbazol-3-yl, 2-benzenesulfonylphenyl, phenyl, pyridin-3-yl, 6-methoxybenzothiazol-2-yl, benzotiazol-2-yl, pyrazol-3-yl, pyridin-4-yl, 2,3,4,5,6-pentafluorophenyl, 3-[1H]-1,2,4-triazolo, 3,5-difluorophenyl, and 2,3,4-trifluorophenyl, where each of $R^3$ and $R^4$ may be —$NH_2$; and where $R^1$ may be $C_1$–$C_{20}$alkyl, and/or aryl; and/or heteroaryl.

In one aspect, the present invention provides a compound of formula (1) selected from (3,5-diamino-4-phenylazo-pyrazol-1-yl)phenylmethanone; 4-(3,5-diamino-4-phenylazopyrazol-1-yl)benzoic acid; 3,5-diamino-1-phenyl-4-phenylazo-pyrazole; 3,5-diamino-1-(4-bromophenyl)-4-phenylazopyrazole; 3,5-diamino-1-(4-fluorophenyl)-4-phenylazopyrazole; and 3,5-diamino-1-methyl-4-phenylazopyrazole.

In another aspect, the present invention provides compounds of formula (2), and compositions comprising a compound of formula (2)

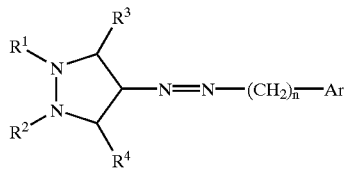

(2)

and stereoisomers, solvates, and pharmaceutically acceptable salts thereof, and a pharmaceutically acceptable carrier, diluent or excipient, where $R^1$ and $R^2$ are selected from H and direct bond; $R^3$ and $R^4$ are selected from —$NH_2$, NHC(=O)$R^5$ and =O; and Ar is an aryl group. In one aspect, Ar is phenyl having one or more substituents selected from alkyl, aryl, heteroalkyl and heteroaryl, where optionally the substituents are selected from benzenesulfonyl, bromide, carbonylethoxy, carbonylmethoxy, chloride, dioxolyl, dioxinyl, ethyl, fluoride, hydroxyl, iodide, iso-propyl, methoxy, methyl, methylthio, phenoxy, phenyl, propyl, and trifluoromethyl. Specific compounds of the invention are 3,5-diamino-4-[(4-fluorophenyl)hydrazono]pyrazole; 3-[N'-(3,5-diaminopyrazol-4-ylidene)hydrazino]-phenol; 3,5-diamino-4-[(3-ethylphenyl)hydrazono]pyrazole; 3,5-diamino-4-[(3-methoxyphenyl)hydrazono]pyrazole; 3,5-diamino-4-[(3-chlorophenyl)hydrazono]-pyrazole; 3,5-diamino-4-[(3-fluorophenyl)hydrazono]pyrazole; 3,5-diamino-4-[(3-fluoro-4-methoxyphenyl)hydrazono]pyrazole; 3,5-diamino-4-[(4-trifluoromethylphenyl)hydrazono]pyrazole; 4-[(3-phenoxyphenyl)hydrazono]pyrazole; 4-[N'-(3,5-diaminopyrazol-4-ylidene)hydrazino]benzoic acid ethyl ester; 3,5-diamino-4-[(biphenyl-2-yl)hydrazono]pyrazole; 3,5-diamino-4-[(2-bromophenyl)hydrazono]-pyrazole; 3,5-d iamino-4-[(3-bromophenyl)hydrazono]pyrazole; 3,5-diamino-4-[(4-bromophenyl)hydrazono]pyrazole; 3,5-diamino-4-[(4-phenoxyphenyl)hydrazono]-pyrazole; 3,5-diamino-4-[(4-iodophenyl)hydrazono]pyrazole; 3,5-diamino-4-[(o-tolyl)hydrazono]pyrazole; 3,5-diamino-4-[(2,6-difluorophenyl)hydrazono]pyrazole; 3,5-diamino-4-[(3,4-difluorophenyl)hydrazono]pyrazole; 3,5-diamino-4-[(benzo[1,3]dioxol-5-yl)hydrazono]pyrazole; 3,5-diamino-4-[(4-methylsulfanylphenyl)hydrazono]pyrazole; 3,5-diamino-4-[(2,3-dihydrobenzo[1,4]dioxin-6-yl)-hydrazono]pyrazole; 3,5-diamino-4-[(3-chloro-4-methoxyphenyl)hydrazono]pyrazole; 3,5-diamino-4-[(3,4-dichlorophenyl)hydrazono]pyrazole; 3,5-diamino-4-[(3,5-dichlorophenyl)hydrazono]-pyrazole; 3,5-diamino-4-[(2-isopropylphenyl)hydrazono]pyrazole; 3,5-diamino-4-[(3,4-dimethoxyphenyl)hydrazono]pyrazole; 3,5-diamino-4-[(3-trifluoromethylphenyl)-hydrazono]pyrazole; 3-[N'-(3,5-diaminopyrazol-4-ylidene)hydrazino]benzoic acid ethyl ester; 3,5-diamino-4-[(3-methoxy-5-trifluoromethylphenyl)-hydrazono]pyrazole; 3,5-diamino-4-[(2-chlorophenyl)hydrazono]pyrazole; 3,5-diamino-4-[(3-iodophenyl)-hydrazono]pyrazole; and 3,5-diamino-4-[(2-benzenesulfonylphenyl)hydrazono]-pyrazole.

In another aspect, the present invention provides compounds of formula (2) wherein Ar is naphthyl optionally having one or more substituents selected from alkyl, aryl, heteroalkyl and heteroaryl, where suitable substituents are benzenesulfonyl, bromide, carbonylethoxy, carbonylmethoxy, chloride, dioxolyl, dioxinyl, ethyl, fluoride, hydroxyl, iodide, iso-propyl, methoxy, methyl, methylthio, phenoxy, phenyl, propyl, and trifluoromethyl; and specific compounds of the invention are: 3,5-diamino-4-[(naphthalen-2-yl)hydrazono]pyrazole; and 3,5-diamino-4-[(4-bromonaphthalen-1-yl)hydrazono]pyrazole.

In compounds of formula (1), the structural moiety

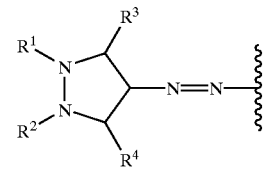

is used to represent a family of tautomeric structures. In part, the particular tautomeric structure(s) encompassed by formula (1) depend on the selected of $R^3$ and $R^4$. When $R^3$ and $R^4$ are each —$NH_2$, then $R^1$ and $R^2$ are —H and/or direct bonds, as shown in the Scheme below.

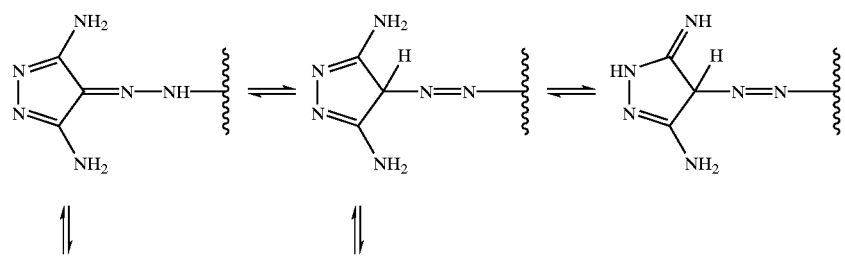

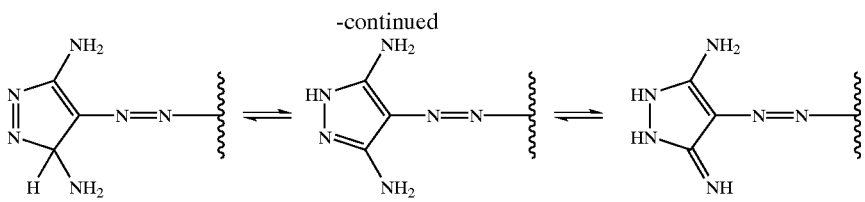

In one embodiment, $R^5$ is selected from carbocyclic and heterocyclic groups, where the carbocyclic and heterocyclic groups preferably contain from 5 to 12 ring atoms. In one embodiment, $R^5$ is a carbocyclic group. In one embodiment, $R^5$ is a heterocyclic group.

In one embodiment, $R^5$ is selected from the carbocyclic groups phenyl and naphthyl. As noted previously, a carbocyclic group may be substituted or unsubstituted. Accordingly, in this embodiment, the phenyl or naphthyl group may be substituted with one or more of, for example, alkyl, alkoxy, hydroxyl, sulfonic acid, carboxylic acid, halogen, amino and acetylamino.

In one embodiment, $R^5$ is selected from a heterocyclic group of the formula

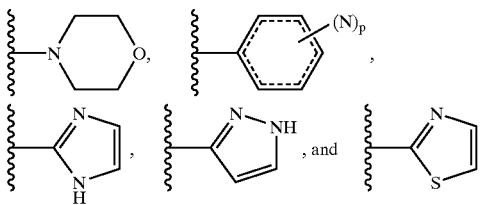

where p is selected from 1, 2 and 3. As used herein, the moiety

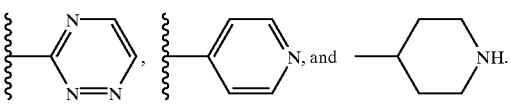

represents a six-membered ring that optionally contains unsaturation and necessarily includes 1, 2 or 3 ring nitrogens. Examples include

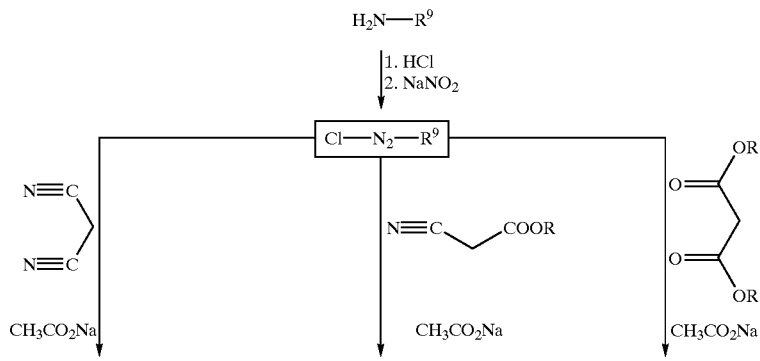

In one embodiment, $R^3$ and $R^4$ are each amino (—$NH_2$) groups. In another embodiment, one of $R^3$ and $R^4$ is an amino group while the other of $R^3$ and $R^4$ is a carbonyl (=O) group. In one embodiment, both of $R^3$ and $R^4$ are carbonyl groups. In one embodiment, n is 0. In another embodiment, n is selected from 0, 1 and 2. In another embodiment, n is selected from 1, 2, 3 and 4.

In one embodiment, the compounds and/or compositions and/or methods of the present invention exclude a compound of formula (1) wherein $R^1$=H, and/or $R^2$=H, and/or $R^3$=amino, and/or $R^4$=amino, and/or n=0, and/or $R^5$=4-methoxyphenyl.

SYNTHETIC METHODS

Compounds as set forth in compositions and methods of the present invention may be prepared by methods disclosed in the literature, and/or as summarized in Scheme 1.

-continued

 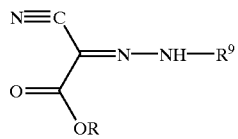 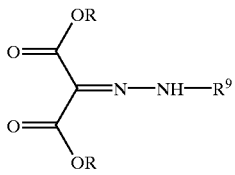

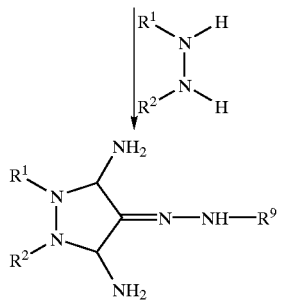 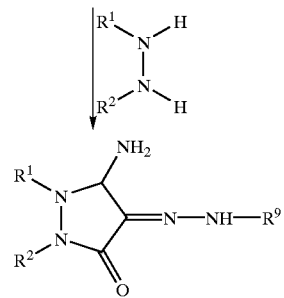 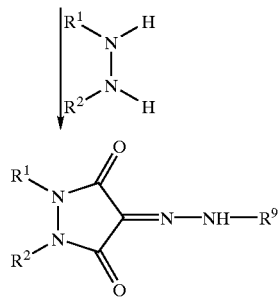

Thus, a primary amine of the formula $H_2N\text{—}R^9$ (where $R^9$ has been selected to represent $\text{—}(CH_2)_n\text{—}R^5$ of formula (1)) is diazotised by treatment sodium nitrite and hydrochloric acid. The intermediate diazo compound (enclosed by a box in Scheme 1) will, in the presence of base (e.g., sodium acetate as shown in Scheme 1) react with compounds containing an active methylene group, i.e., a compound including a methylene group ($\text{—}CH_2\text{—}$) flanked by electron withdrawing groups such as cyano ($\text{—}CN$) and/or ester ($\text{—}COOR$), to provide an azo compound. This azo compound may be reacted with a hydrazine derivative to provide compounds of the present invention.

In Scheme 1, $R^1$ and $R^2$ are each preferably hydrogen. However, either or both of $R^1$ and $R^2$ may be an alkyl group.

PHARMACEUTICAL FORMULATIONS

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition. as a solution in sterile water, normal saline or another pharmaceutically acceptable carrier.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant containing the inhibitory compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided inhibitory compounds and other cytotoxic agents has the advantages that the required dosages for the individual drugs is lower, and the effect of the different drugs complementary. Depending on the patient and condition being treated and on the administration route, the subject inhibitory compounds may be administered in dosages of 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

METHODS OF USE

The subject compounds are administered to a subject having a hyperproliferative disorders, e.g. to inhibit tumor growth, to inhibit angiogenesis, to decrease inflammation associated with a lymphoproliferative disorder, to inhibit graft rejection, or neurological damage due to tissue repair, etc. The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g. to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one h and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes Type I and Type II, immunological disorders, e.g. autoimmune and immunodeficiency diseases; hyperproliferative disorders, which may include psoriasis, arthritis, inflammation, angiogenesis, endometriosis, scarring, cancer, etc.

The compounds of the present invention are active in inhibiting purified kinase proteins, i.e. there is a decrease in the phosphorylation of a specific substrate in the presence of the compound. A protein kinase of particular interest is integrin linked kinase (ILK). ILK is a serine threonine kinase. The DNA and predicted amino acid sequence may be accessed at Genbank, no. U40282, or as published in Hannigan et al. (1996) *Nature* 379:91–96. ILK regulates integrin extracellular activity (ECM interactions) from inside the cell via its direct interaction with the integrin subunit. Interfering with ILK activity allows the specific targeting of integrin function, while leaving other essential signaling pathways intact. Increased levels of cellular ILK activity short circuits the normal requirement for adhesion to extracellular membrane in regulating cell growth. Thus, inhibiting ILK activity may inhibit anchorage-independent cell growth.

It is also known that many cell types undergo apoptosis if the appropriate contacts with extracellular matrix proteins are not maintained (anoikis). The induction of apoptosis by the subject compounds in such cells predicts an association with the ILK signaling pathway.

The compounds of the present invention bind to protein kinases at a high affinity, and find use as affinity reagents for the isolation and/or purification of such kinases. Affinity chromatography is used as a method of separating and purifying protein kinases and phosphatases using the biochemical affinity of the enzyme for inhibitors that act on it. The compounds are coupled to a matrix or gel. Preferably a microsphere or matrix is used as the support. Such supports are known in the art and commercially available. The inhibitor coupled support is used to separate an enzyme that binds to the inhibitor from a complex mixture, e.g. a cell lysate, that may optionally be partially purified. The sample mixture is contacted with the inhibitor coupled support under conditions that minimize non-specific binding. Methods known in the art include columns, gels, capillaries, etc. The unbound compounds are washed free of the resin, and the bound proteins are then eluted in a suitable buffer.

The compounds of the invention may also be useful as reagents for studying signal transduction or any of the clinical disorders listed throughout this application.

HYPER-PROLIFERATIVE DISORDERS OF INTEREST

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature. Angiogenesis may be inhibited by affecting the cellular ability to interact with the extracellular environment and to migrate, which is an integrin-specific function, or by regulating apoptosis of the endothelial cells. Integrins function in cell-to-cell and cell-to-extracellular matrix (ECM) adhesive interactions and transduce signals from the ECM to the cell interior and vice versa. Since these properties implicate integrin involvement in cell migration, invasion, intra- and extra-vasation, and platelet interaction, a role for integrins in tumor growth and metastasis is obvious.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary. carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ is the most common type of noninvasive breast cancer. In, DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenus routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

In Vitro Screen

Compounds were screened using a series of disease related kinase targets, such as integrin linked kinase-1. Synthesized libraries of compounds are tested against each of the targets to find compounds that inhibit one of the targets preferentially. The desired in vitro potency of the inhibitor is such that the compound is useful as a therapeutic agent, i.e. in the nanomolar or micromolar range.

Inhibition of the targets is measured by scintillation counting; the incorporation of radioactive phosphate onto a specific substrate which is immobilized onto a filter paper at the end of the assay. To provide meaningful measurements of inhibition, the assays are performed both in the absence and presence of specific and known inhibitors, and the amount of incorporated radioactivity is compared to provide a baseline measurement.

The baseline activity is the amount of radioactivity incorporated in the absence of inhibitor. The amount of radioactivity incorporated in the presence of an inhibitor is called the 'sample activity', and the % inhibition is expressed by the following formula:

% inhibition=100−sample activity/baseline activity*100)

and is usually expressed in conjunction with the compound concentration. By using a range of inhibitor concentrations, the $IC_{50}$ of an inhibitor is estimated (i.e. the concentration at which enzymatic activity is reduced by 50%). The $IC_{50}$ of various compounds against a particular target can be compared, where a lower $IC_{50}$ indicates a more potent compound.

Materials and Methods

Inhibition Assay: Compounds listed in Table 1 were lyophilized and stored at −20° C. Stock solutions were made by weighing out the compounds and dissolving them in dimethyl sulfoxide (DMSO) to a standard concentration, usually 20 mM, and stored at −20° C. The compounds were diluted to a starting intermediate concentration of 250 μM in 1% DMSO, then serially diluted across a row of a 96 well plate using serial 2 fold dilution steps. Diluted 100% DMSO was used as a negative control. 5 μl of each compound dilution were robotically pipetted to Costar serocluster plates maintaining the same plate format. All assays consisted of the following volumes:

5 μl diluted compound

10 μl enzyme preparation

5 μl substrate

5 μl assay ATP and were then incubated 15 min at room temperature.

From each reaction, 10 μl of reaction mix was spotted onto Millipore Multiscreen-PH opaque plates and washed 2×10 min in 1% phosphoric acid. The plates were dried for at 40° C. for 30 min, then the substrate phosphate complexes were quantitated by scintillation counting. These Millipore plates are in a 96 well format with immobilized P81 phosphocellulose membranes. Both the phosphorylated and non-phosphorylated form of the substrate bind to the membrane while ATP (unincorporated phosphate) is removed in the subsequent wash steps. Results are shown in Table 1 below.

Integrin Linked Kinase: The target integrin linked kinase is a full-length recombinant protein expressed in sF9 insect cells by baculovirus infection. The ILK1 substrate is CKRRRLASLR-amide.

Recombinant ILK protein was expressed using cultured insect cells and a baculovirus expression system. Standard techniques for DNA manipulation were used to produce recombinant DNA molecules and baculoviruses (Sambrook. J., Fritsch, E. F. and Maniatis, T. 1989. Molecular cloning, a laboratory manual. Second edition. Cold Spring Harbor Laboratory Press. NY; Crossen, R. and Gruenwald, S. 1998. Baculovirus expression Vector System Manual. $5^{th}$ Edition. Pharmingen, San Diego, Calif.) but the isolation of active ILK required some ingenuity.

The ILK open reading frame (Hannigan et al., supra.), excluding the 5' and 3' untranslated regions, was inserted into the baculovirus transfer vector pAcG2T (Pharmingen) to produce a GST fusion protein under the control of the strong AcNPV polyhedrin promoter. A large scale plasmid preparation of the resulting transfer construct was made using a Qiagen Plasmid Midi Kit. This ILK transfer construct was then co-transfected with BaculoGold DNA (Pharmingen) into Sf9 insect cells (Invitrogen) and a high titre preparation of GST-ILK recombinant baculovirus was produced by amplification in Sf9 cells. Liter scale expression of GST-ILK recombinant protein was done in 1000 ml spinner flasks (Bellco) by infection of Hi5 insect cells (Invitrogen) grown in Ex-Cell 400 Serum Free Media (JRH Biosciences) at a multiplicity of infection of approximately 5. The cells were harvested three days after infection and lysed in Hypotonic Lysis Buffer (HLB; 10 mM imidazole, 5 mM EDTA, 0.1% β-mercaptoethanol, 10 ug/ml PMSF, 1 mM benzamidine) by sonication. The lysate was centrifuged at 10,000 g for 20 min and the supernatant was discarded. The pellet was washed twice in HLB and then washed twice in High Salt Buffer ("HSB"; 500 mM NaCl, 10 mM imidazole, 5 mM EDTA, 0.1% β-mercaptoethanol, 10 ug/ml PMSF, 1 mM benzamidine). The pellet was then resuspended in DNAse-ATP Buffer ("DAB"; 10 mM $MgCl_2$, 1 mM $MnCl_2$, β-methyl aspartic acid, 2 mM NaF, 0.55 mg/ml ATP, 1 ug/ml DNAse I, 1% NP-40, 10 mM imidazole, 5 mM EDTA, 0.1% β-mercaptoethanol, 10 ug/ml PMSF, 1 mM benzamidine) and stirred for 30 min at room temperature, and then centrifuged at 10,000×g for 20 min. The pellet was resuspended in High Salt Detergent buffer ("HDB"; 1% NP-40, 1% Triton X-100, 500 mM NaCl, 10 mM imidazole, 5 mM EDTA, 0.1% β-mercaptoethanol, 10 ug/ml PMSF, 1 mM benzamidine), stirred for 30 min at room temperature, and then centrufuged at 10,000 g for 20 min. The pellet was then washed once in each of HDB, HSB, and HLB, centrifuging at 10,000 g each time. Finally, the pellet was resuspended in HLB.

The recombinant ILK expressed in insect cells with a baculovirus system was solubilized by treating the insoluble ILK protein with DNAse I and detergents. This produced an ILK protein preparation in the form of a microparticle suspension. This preparation had a high specific activity and was amenable to automated kinase assays.

TABLE 1

Activity of Analogs of KP-15792

| Codes | Chemical Name | Structure | MW | IC$_{50}$(μM) |
|---|---|---|---|---|
| KP-15792 | 3,5-diamino-4-(p-methoxyphenyl)hydrazono-pyrazole | 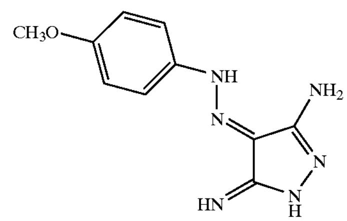 | 232.24 | 1 |
| KP-23194 | 3,5-diamino-4-phenylhydrazonopyrazole | 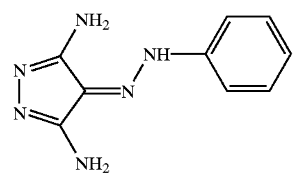 | 202.21 | 0.6 |
| KP-23195 | 3,5-diamino-4-(p-methylphenyl)hydrazonopyrazole | 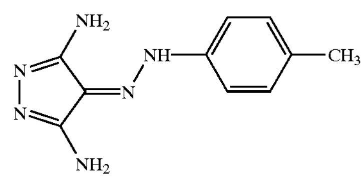 | 216.24 | 5.3 |
| KP-23197 | 3,5-diamino-4-(3-hydroxy-4-methoxyphenyl)hydrazonopyrazole | 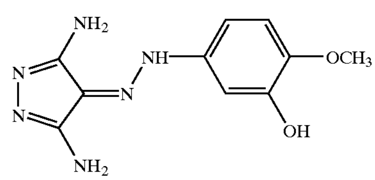 | 248.24 | 4 |
| KP-23198 | 3-amino-4-phenylazo-2-pyrazolin-5-one | 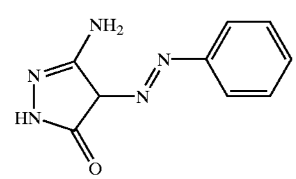 | 203.20 | 17.1 |
| KP-23199 | 3-amino-4-(p-methylphenylazo)-2-pyrazolin-5-one | 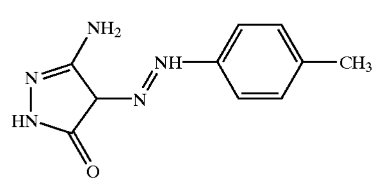 | 217.23 | >20 |
| KP-23200 | 3-amino-4-(p-methoxyphenylazo)-2-pyrazolin-5-one | 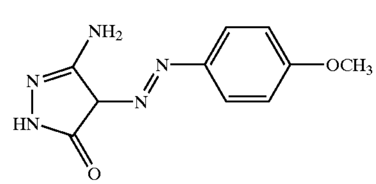 | 233.22 | >20 |

TABLE 1-continued

Activity of Analogs of KP-15792

| Codes | Chemical Name | Structure | MW | IC$_{50}$($\mu$M) |
|---|---|---|---|---|
| KP-23201 | 3-amino-4-(3-hydroxy-4-methoxyphenylazo)-2-pyrazolin-5-one | 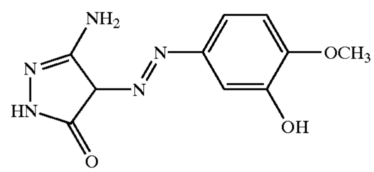 | 249.22 | 18 |
| KP-23202 | 4-phenylhydrazonopyrazolin-3,5-dione | 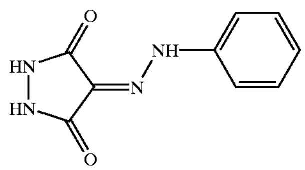 | 204.18 | >20 |
| KP-23203 | 4-(p-methylphenyl)hydrazonopyrazolin-3,5-dione | 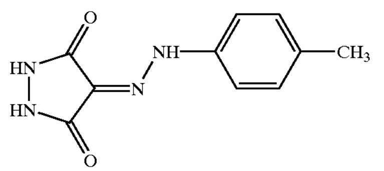 | 218.21 | >20 |
| KP-23204 | 4-(p-methoxyphenyl)hydrazonopyrazolin-3,5-dione | 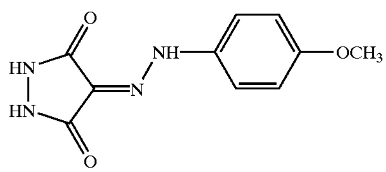 | 234.21 | >20 |
| KP-23205 | 4-(3-hydroxy-4-methoxyphenyl)hydrazonopyrazolin-3,5-dione | 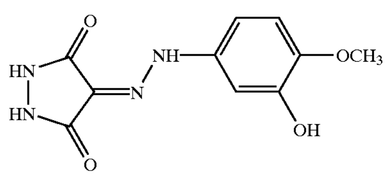 | 250.21 | >20 |
| KP-27288 | 4-[N'-(3,5-diaminopyrazole-4-ylidene)hydrazino]benzenesulfonic acid | 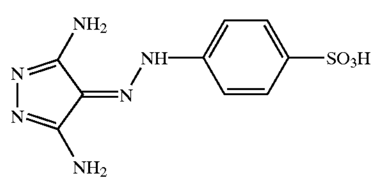 | 282.27 | >20 |
| KP-27289 | 3,5-diamino-4-morpholinylhydrazonopyrazole | 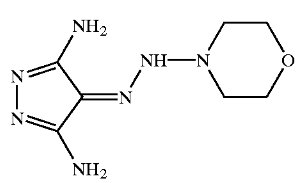 | 211.22 | 9.6 |
| KP-27290 | 3,5-diamino-4-(2-morpholinylethyl)hydrazonopyrazole | 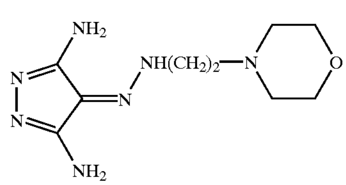 | 239.28 | 8.2 |

TABLE 1-continued

Activity of Analogs of KP-15792

| Codes | Chemical Name | MW | IC$_{50}$($\mu$M) |
|---|---|---|---|
| KP-27291 | 3,5-diamino-4-(2-imidazolyl)hydrazonopyrazole | 192.18 | 28 |
| KP-27292 | 3,5-diamino-4-(3-pyrazolyl)hydrazonopyrazole | 192.18 | 8 |
| KP-27293 | 3,5-diamino-4-(2-thiazolyl)hydrazonopyrazole | 209.22 | 0.9 |
| KP-27386 | 3,5-diamino-4-(4-piperidinylmethyl)hydrazonopyrazole | 223.28 | 13 |
| KP-27387 | 3,5-diamino-4-(3-[1,2,4]triazinyl)hydrazonopyrazole | 205.18 | >20 |
| KP-27294 | 3,5-diamino-4-(1-naphthyl)hydrazonopyrazole | 252.27 | 0.6 |
| KP-27295 | 4-[N'-(3,5-Diaminopyrazol-4-ylidene)hydrazino]naphthalene-1-sulfonic acid | 332.33 | 19.3 |
| KP-27388 | 4-[N'-(3,5-diaminopyrazol-4-ylidene)hydrazino]benzoic acid | 246.22 | 13 |

TABLE 1-continued

Activity of Analogs of KP-15792

| Codes | Chemical Name | Structure | MW | IC$_{50}$($\mu$M) |
|---|---|---|---|---|
| KP-27389 | 3,5-diamino-4-(p-hydroxyphenyl)hydrazonopyrazole | 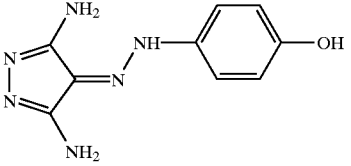 | 218.21 | >20 |
| KP-27390 | 3,5-diamino-4-(p-chlorophenyl)hydrazonopyrazole | 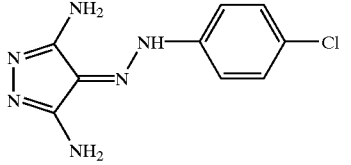 | 236.66 | 1.2 |
| KP-27391 | 3,5-diamino-4-(p-(n-propyl)phenyl)hydrazonopyrazole | 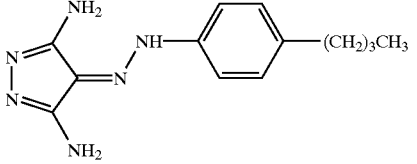 | 258.32 | 4.6 |
| KP-27392 | 3,5-diamino-4-(p-acetoaminophenyl)hydrazonopyrazole | 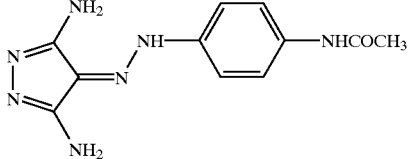 | 274.3 | 5 |
| KP-27393 | 3,5-diamino-4-(2-hydroxynaphthyl)hydrazonopyrazole | 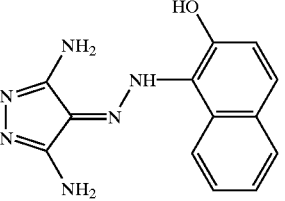 | 268.27 | 3 |

Example 4

Synthesis of 3,5-Diamino-4-(p-methoxyphenyl)hydrazonopyrazole

Unless otherwise stated, chemical reactants and reagents were obtained from standard chemical supply houses, such as Aldrich (Milwaukee, Wis.; www.aldrich.sial.com); and Lancaster Synthesis, Inc. (Windham, N.H.; www.lancaster.co.uk).

To a flask containing p-anisidine (5.46 g, 44.3 mmol) and concentrated HCl solution (11 mL) in 75 mL of water, cooled in an ice water bath, was added sodium nitrite solution (4.57 g, 66.3 mmol). The resulting mixture was then added to a solution of malononitrile (4.79 g, 72.6 mmol) in a mixture of MeOH (12 mL) and water (25 mL). A large quantity of yellow solid quickly precipitated. The mixture was stirred for about 30 minutes at room temperature. The solid was collected and purified by recrystallization in hot EtOH. The product (6.17 g, 70%) was obtained as a yellow solid.

To a suspension of the yellow solid (2.00 g) prepared above in 10 mL of EtOH was added hydrazine hydrate (2.0 mL). This mixture was refluxed for about 3 h. The yellow solid was collected and purified by recrystallization in hot EtOH. The product was isolated as yellow cotton like solid (1.50 g, 65%). m.p.: 263–265° C. $^1$H NMR (ppm, in DMSO-d$_6$): 10.73 (s, br, 1H), 7.69 (m, 2H), 6.99 (m, 2H), 6.00 (s, br, 4H), 3.81 (s, 3H). $^{13}$C NMR (ppm, in DMSO-d$_6$): 158.4, 147.6, 121.7, 114.0, 113.4, 99.9, 55.3. FTIR (cm$^{-1}$, KBr pellet): 3401, 3301, 3187, 1603, 562, 1498, 1248, 1033, 828. Mass spectrometry (m/e, El): 232 (M$^+$, 100%). Elemental analysis for C$_{10}$H$_{12}$N$_6$O (obtained/calcd.): C 52.28/51.72, H 5.18/5.21, N 35.88/36.19.

Example 5

Additional Syntheses According To Procedure of Example 4

The following compounds were synthesized, using malononitrile, following essentially the same procedure as described above in Example 4:

3,5-diamino-4-phenylhydrazonopyrazole;
3,5-diamino-4-(p-methylphenyl)hydrazonopyrazole;
3,5-diamino-4-(3-hydroxy-4-methoxyphenyl)hydrazonopyrazole;

4-[N'-(3,5-Diaminopyrazole-4-ylidene)hydrazino] benzenesulfonic acid;

3,5-diamino-4-morpholinylhydrazonopyrazole;

3,5-diamino-4-(2-morpholinylethyl)hydrazonopyrazole;

3,5-diamino-4-(2-imidazolyl)hydrazonopyrazole;

3,5-diamino-4-(3-pyrazolyl)hydrazonopyrazole;

3,5-diamino-4-(2-thiazolyl)hydrazonopyrazole;

3,5-diamino-4-(3-naphthyl)hydrazonopyrazole;

3,5-diamino-4-(1-(3-sulfonyl)naphthalyl) hydrazonopyrazole;

3,5-diamino-4-(4-piperidinylmethyl)hydrazonopyrazole;

3,5-diamino-4-(3-[1,2,4]triazinyl)hydrazonopyrazole;

4-[N'-(3,5-diaminopyrazol-4-ylidene)hydrazino] naphthalene-1-sulfonic acid;

4-[N'-(3,5-diaminopyrazol-4-ylidene)hydrazino]benzoic acid;

3,5-diamino-4-(p-hydroxyphenyl)hydrazonopyrazole;

3,5-diamino-4-(-chlorophenyl)hydrazonopyrazole;

3,5-diamino-4-(p-(n-propyl)phenyl)hydrazonopyrazole;

3,5-diamino-4-(p-acetoaminophenyl)hydrazonopyrazole; and 3,5-diamino-4-(2-hydroxynaphthyl)hydrazonopyrazole.

Example 6

Additional Syntheses According To Procedure of Example 4, Using Ethyl Cyanoacetate The following compounds were synthesized using ethyl cyanoacetate instead of malononitrile, but otherwise following essentially the same procedure as described above in Example 4:

3-amino-4-phenylazo-2-pyrazolin-5-one;

3-amino-4-(p-methylphenylazo)-2-pyrazolin-5-one;

3-amino-4-(p-methoxyphenylazo)-2-pyrazolin-5-one; and 3-amino-4-(3-hydroxy-4-methyoxyphenylazo)-2-pyrazolin-5-one.

Example 7

Additional Syntheses According To Procedure of Example 4, Using Diethyl Malonate The following compounds were synthesized using diethyl malonate instead of malononitrile, but otherwise following essentially the same procedure as described above in Example 4:

4-phenylhydrazonopyrazolin-3,5-dione;

4-(p-methylphenyl)hydrazonopyrazolin-3,5-dione;

4-(p-methoxyphenyl)hydrazonopyrazolin-3,5-dione; and 4-(3-hydroxy-methyoxyphenyl)hydrazonopyrazolin-3,5-dione.

Example 8

Synthesis of 3,5-Diamino-4-[(4-fluorophenyl) hydrazono]pyrazole

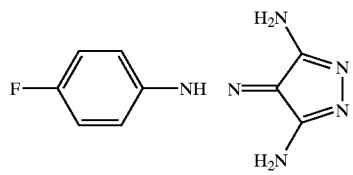

4-Fluoroaniline (95 µL, 1.0 mmol) was weighed into a 25 mL test tube. Deionized water (1–2 mL) was added to the test tube and the suspension was cooled to below 5° C. in an ice bath. Concentrated HCl (250 µL, 3.0 mmol) was added dropwise to the mixture. If the solution remained inhomogeneous, DMF was added until all the solids had dissolved (0–2 mL). An aqueous sodium nitrite solution (290 µL of a 5.25 M solution, 1.5 mmol) was added dropwise to this mixture and allowed to stir for approximately 5 minutes. The resulting clear pale yellow solution was then added dropwise to a second 25 mL test tube containing 1.4 mL of an ice cold aqueous solution which was 1.82 M (2.3 mmol) in sodium acetate trihydrate and 1.09 M (1.5 mmol) in malononitrile. A precipitate formed immediately. The reaction solution was stirred for 1–2 hrs while warming to room temperature. The solution was then filtered and the precipitate was washed twice with 5 mL of deionized water. The product was dried overnight under vacuum to yield 169 mg (90%) of the desired malononitrile derivative as a yellow solid. A portion of this solid (94 mg, 0.5 mmol) was weighed into a 25 mL test tube. Anhydrous ethanol (1.5 mL) was added and the slurry was heated to 75° C. Once the solid had dissolved, hydrazine hydrate (1 mmol) was added dropwise via micropipette. A precipitate usually formed within 10 minutes. The reaction was monitored for the disappearance of the starting material by TLC, as well as, for the appearance of a more polar spot due to the product. Once the reaction was complete, the solution was allowed to cool to room temperature. The solid was isolated by filtration, washed with ethanol, and dried to yield 17 mg (15%) of the title compound as a mustard coloured solid.

Example 9

Synthesis of 3-[N'-(3,5-Diaminopyrazol-4-ylidene) hydrazino]phenol

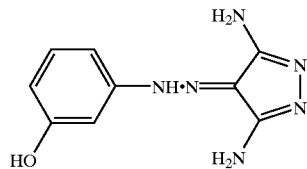

3-[N'-(3,5-Diaminopyrazol-4-ylidene)hydrazino]phenol was prepared using 93 mg (0.5 mmol) of 2-[(3-hydroxyphenyl)hydrazono]malononitrile, which was derived from 3-aminophenol (109 mg, 1.0 mmol) and malononitrile (1.5 mmol) as described in Example 8, and hydrazine hydrate. After heating for 4 hrs, a small amount of solid had formed. The solid was filtered off and the filtrate was concentrated to a gummy black solid. This material was dissolved in ethyl acetate and a small amount of gummy solid was precipitated from the solution by the addition of hexanes. The solid was removed by filtration and the filtrate was again concentrated. The resulting solid was purified by flash chromatography eluting with methylene chloride/methanol (7:1) to yield 45 mg (33%) of the title compound as a black solid.

EXAMPLE 10

Synthesis of 3,5-Diamino-4-[(3-ethylphenyl)hydrazono]pyrazole

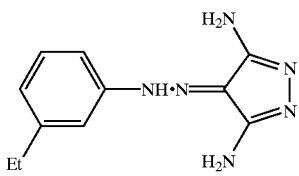

3,5-Diamino-4-[(3-ethylphenyl)hydrazono]pyrazole was prepared using 99 mg (0.5 mmol) of 2-[(3-ethylphenyl)hydrazono]malononitrile, which was derived from 3-ethylaniline (124 μL, 1.0 mmol) and malononitrile (1.5 mmol) as described in Example 8, and hydrazine hydrate. Precipitate formed in the reaction tube approximately 10 min after the addition of hydrazine hydrate. The resulting solid was isolated by filtration, precipitated from an ethyl acetate solution by the addition of hexanes, and dried to yield 12 mg (10%) of the title compound as a yellow solid.

Example 11

Synthesis of 3,5-Diamino-4-[(3-methoxyphenyl)hydrazono]pyrazole

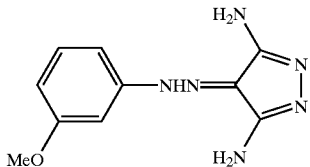

The title compound was prepared using 100 mg (0.5 mmol) of 2-[(3-methoxyphenyl)-hydrazono]malononitrile, which was derived from m-anisidine (112 μL, 1.0 mmol) and malononitrile (1.5 mmol) as described in Example 8, and hydrazine hydrate. Precipitate formed in the reaction tube approximately 10 min after the addition of hydrazine hydrate. The resulting solid was isolated by filtration, recrystallized from ethanol, and dried to yield 25 mg (22%) of the title compound as a brownish orange solid.

Example 12

Synthesis of 3,5-Diamino-4-[(3-clorophenyl)hydrazono]pyrazole

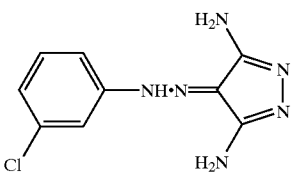

This compound was prepared using 102 mg (0.5 mmol) of 2-[(3-chlorophenyl)-hydrazono]malononitrile, which was derived from 3-chloroaniline (106 μL, 1.0 mmol) and malononitrile (1.5 mmol) as, described in Example 8, and hydrazine hydrate. Precipitate formed in the reaction tube approximately 5 min after the addition of hydrazine hydrate. The resulting solid was isolated by filtration, precipitated from an ethyl acetate solution by the addition of hexanes, and dried to yield 17 mg (14%) of the title compound as a yellow solid. $^1$H NMR (ppm, DMSO-$d_6$): 5.98 (br, s, 2H), 6.38 (br, s, 2H), 7.18 (d, 1H), 7.40 (t, 1H), 7.60 (d, 1H), 7.69 (s, 1H), 10.78 (s,1H).

Example 13

Synthesis of 3,5-Diamino-4-[(3-fluorophenyl)hydrazono]pyrazole

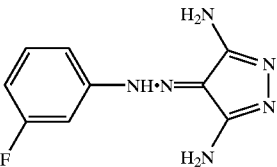

This compound was prepared using 94 mg (0.5 mmol) of 2-[(3-fluorophenyl)-hydrazono]malononitrile, which was derived from 3-fluoroaniline (96 μL, 1.0 mmol) and malononitrile (1.5 mmol) as described in Example 8, and hydrazine hydrate. Precipitate formed in the reaction tube approximately 5 min after the addition of hydrazine hydrate. The resulting solid was isolated by filtration, washed with ethanol, and dried to yield 41 mg (37%) of the title compound as a yellow solid. $^1$H NMR (ppm, DMSO-$d_6$): 6.2 (br s, 4H), 7.0 (t, 1H), 7.35–7.62 (m, 3H), 10.80 (s, 1H).

Example 14

Synthesis of 3,5-Diamino-4-[(3-methoxyphenyl)hydrazono]pyrazole

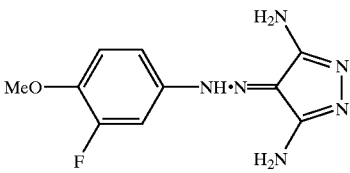

This compound was prepared using 109 mg (0.5 mmol) of 2-[(3-fluoro-4-methoxyphenyl)hydrazono]malononitrile, which was derived from 3-fluoro-p-anisidine (141 mg, 1.0 mmol) and malononitrile (1.5 mmol) as described in Example 8, and hydrazine hydrate. Precipitate formed in the reaction tube immediately after the addition of hydrazine hydrate. The resulting solid was isolated by filtration, washed with ethanol, and dried to yield 85 mg (68%) of the title compound as a mustard coloured solid.

Example 15

Synthesis of 3,5-Diamino-4-[(naphthalen-2-yl)hydrazono]pyrazole

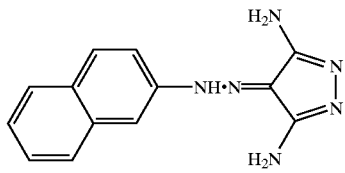

The title compound was prepared using 110 mg (0.5 mmol) of 2-[(naphthalen-2-yl)hydrazono]malononitrile, which was derived from 2-aminonaphthalene (143 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 86 mg (67%) of the title compound as a tan coloured solid.

Example 16

Synthesis of 3,5-Diamino-4-[(4-trifluoromethylphenyl)hydrazono]pyrazole

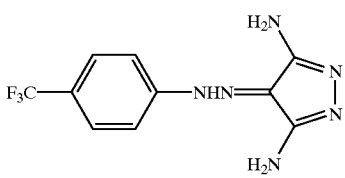

This compound was prepared using 119 mg (0.5 mmol) of 2-[(4-trifluoromethylphenyl)-hydrazono]malononitrile, which was derived from 4-(trifluoromethyl)aniline (126 μL, 1.0 mmol) and malononitrile (1.5 mmol) as described in Example 8, and hydrazine hydrate. No precipitate had formed after heating at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 67 mg (50%) of the title compound as a greenish brown solid. $^1$H NMR (ppm, DMSO-$d_6$): 6.03 (br s, 2H), 6.48 (br s, 2H), 7.63 (d, 2H), 7.80 (d, 2H), 10.80 (br s, 1H).

Example 17

Synthesis of 4-[(3-phenoxyphenyl)hydrazono]pyrazole

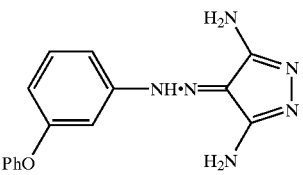

The title compound was prepared using 131 mg (0.5 mmol) of 2-[(3-phenoxyphenyl)-hydrazono]malononitrile, which was derived from 3-phenoxyaniline (185 mg, 1.0 mmol) and malononitrile (1.5 mmol) as described in Example 8, and hydrazine hydrate. Precipitate formed in the reaction tube approximately 5 min after the addition of hydrazine hydrate. The resulting solid was isolated by filtration, recrystallized from ethanol, and dried to yield 87 mg (59%) of the title compound as a mustard coloured solid.

Example 18

Synthesis of 4-[(N'-(3,5-diaminopyrazol-4-ylidene)hydrazino]benzoic Acid Ethyl Ester

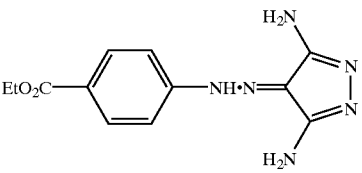

This compound was prepared using 121 mg (0.5 mmol) of 4-(N'-dicyanomethylene-hydrazino)benzoic acid ethyl ester, which was derived from ethyl 4-aminobenzoate (165 mg, 1.0 mmol) and malononitrile (1.5 mmol) as described in Example 8, and hydrazine hydrate. The hydrazine hydrate was added to the solution at a temperature of 75° C. The solution cleared briefly and then a precipitate formed. The resulting solid was isolated by filtration, washed with ethanol, and dried to yield 45 mg (33%) of the title compound as a yellow solid.

Example 19

Synthesis of 3,5-Diamino-4-[(biphenyl-2-yl)hydrazono]pyrazole

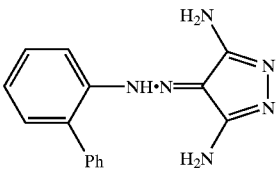

This compound was prepared using 123 mg (0.5 mmol) of 2-[(biphenyl-2-yl)hydrazono]-malononitrile, which was derived from 2-aminobiphenyl (169 mg, 1.0 mmol) and malononitrile (1.5 mmol) as described in Example 8, and hydrazine hydrate. Precipitate formed in the reaction tube immediately after the addition of the hydrazine hydrate then the solution cleared. Very little solid remained after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 85 mg (61%) of the title compound as an orange solid.

Example 20

Synthesis of 3,5-Diamino-4-[(2-bromophenyl)hydrazono]pyrazole

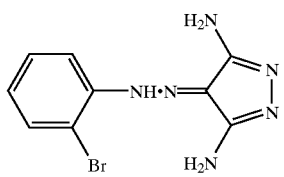

This compound was prepared using 125 mg (0.5 mmol) of 2-[(2-bromophenyl)-hydrazono]malononitrile, which was derived from 2-bromoaniline (172 mg, 1.0 mmol) and malononitrile (1.5 mmol) as described in Example 8, and hydrazine hydrate. Very little solid had formed after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 102 mg (73%) of the title compound as an orange solid.

Example 21

Synthesis of 3,5-Diamino-4-[(3-bromophenyl)hydrazono]pyrazole

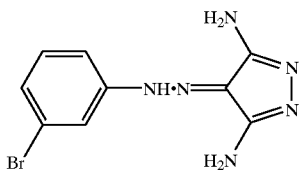

This compound was prepared using 125 mg (0.5 mmol) of 2-[(3-bromophenyl)-hydrazono]malononitrile, which was derived from 3-bromoaniline (172 mg, 1.0 mmol) and malononitrile (1.5 mmol) as. described in Example 8, and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 93 mg (66%) of the title compound as an orange solid. $^1$H NMR (ppm, DMSO-d$_6$): 6.2 (br s, 4H), 7.21–7.32 (m, 2H), 7.50–7.62 (m, 1H), 7.90 (s, 1H), 10.71 (s, 1H).

Example 22

Synthesis of 3,5-Diamino-4-[(4-bromophenyl)hydrazono]pyrazole

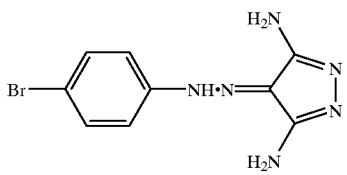

This compound was prepared using 125 mg (0.5 mmol) of 2-[(4-bromophenyl)-hydrazono]malononitrile, which was derived from 4-bromoaniline (172 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 109 mg (78%) of the title compound as a yellow solid. $^1$H NMR (ppm, DMSO-d$_6$): 6.15 (br s, 4H), 7.52 (d, 2H), 7.61 (d, 2H), 10.71 (s, 1H).

Example 23

Synthesis of 3,5-Diamino-4-[(4-phenoxyphenyl)hydrazono]pyrazole

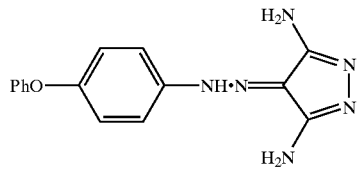

This compound was prepared using 131 mg (0.5 mmol) of 2-[(4-phenoxyphenyl)-hydrazono]malononitrile, which was derived from 4-phenoxyaniline (185 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 90 mg (61%) of the title compound as an orange solid.

Example 24

Synthesis of 3,5-Diamino-4-[(4-iodophenyl)hydrazono]pyrazole

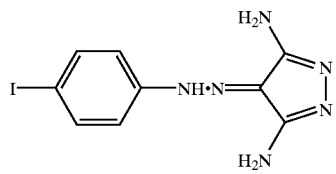

This compound was prepared using 148 mg (0.5 mmol) of 2-[(4-iodophenyl)hydrazono]-malononitrile, which was derived from 4-iodoaniline (219 mg, 101.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 114 mg (70%) of the title compound as a yellow solid.

Example 25

Synthesis of 3,5-Diamino-4-[(4-bromonaphthalen-1-yl)hydrazono]pyrazole

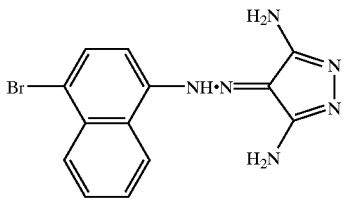

This compound was prepared using 149 mg (0.5 mmol) of 2-[(4-bomonaphthalen-1-yl)-hydrazono]malononitrile, which was derived from 1-amino-4-bromonaphthalene (222 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared. Very little solid had formed after heating the reaction at 75° C. for 1 hr, however, analysis of the reaction solution by TLC indicated that no starting material remained. The solution was allowed to cool to room temperature and the solvent was evaporated. The residue was dissolved in methanol and then precipitated by the addition of water. The resulting solid was isolated by filtration and dried to yield 42 mg (26%) of the title compound as a brown solid.

Example 26

Synthesis of 3,5-Diamino-4-[(o-tolyl)hydrazono]pyrazole

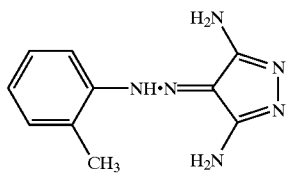

This compound was prepared using 92 mg (0.5 mmol) of 2-(o-tolylhydrazono)-malononitrile, which was derived from 4-toluidine (107 μL, 1.0 mmol) and malononitrile (1.5 mmol) as described in Example 8, and hydrazine hydrate. Very little solid had formed after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 43 mg (40%) of the title compound as a yellow solid.

Example 27

Synthesis of 3,5-Diamino-4-[(2,6-difluorophenyl)hydrazono]pyrazole

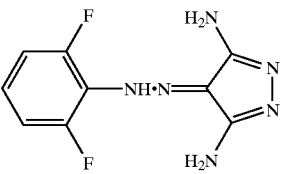

This compound was prepared using 103 mg (0.5 mmol) of 2-[(2,6-difluorophenyl)-hydrazono]malononitrile, which was derived from 2,6-difluoroaniline (108 μL, 1.0 mmol) and malononitrile (1.5 mmol) as described in Example 8, and hydrazine hydrate. Precipitate formed in the reaction tube approximately 10 min after the addition of hydrazine hydrate. The resulting solid was isolated by filtration, washed with ethanol, and dried to yield 44 mg (37%) of the title compound as an orange solid.

Example 28

Synthesis of 3,5-Diamino-4-[(3,4-difluorophenyl)hydrazono]pyrazole

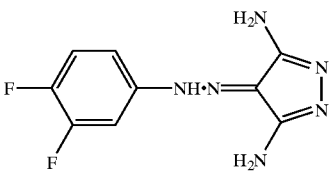

This compound was prepared using 103 mg (0.5 mmol) of 2-[(3,4-difluorophenyl)-hydrazono]malononitrile, which was derived from 3,4-difluoroaniline (99 μL, 1.0 mmol) and malononitrile (1.5 mmol) as described in Example 8, and hydrazine hydrate. Precipitate formed in the reaction tube approximately 5 min after the addition of hydrazine hydrate. The resulting solid was isolated by filtration, washed with ethanol, and dried to yield 45 mg (38%) of the title compound as a yellow solid. $^1$H NMR (ppm, DMSO-$d_6$): 6.18 (br s, 4H), 7.28–7.55 (m, 2H), 7.70–7.82 (m, 1H), 10.80 (br s, 1H).

Example 29

Synthesis of 3,5-Diamino-4-[(benzo[1,3]dioxol-5-yl)hydrazono]pyrazole

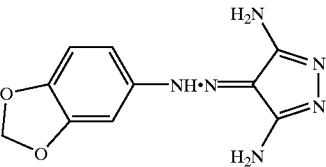

This compound was prepared using 107 mg (0.5 mmol) of 2-(benzo[1,3]dioxol-5-yl-hydrazono)malononitrile, which was derived from 3,4-methylenedioxyaniline (137 mg, 1.0 mmol) and malononitrile (1.5 mmol) as described in Example 8, and hydrazine hydrate. Precipitate formed in the reaction tube approximately 10 min after the addition of hydrazine hydrate. The resulting black solid was isolated by filtration, dissolved in acetone, and hexanes was added to precipitate a small amount of black solid. The solid was removed by filtration and the filtrate was concentrated to yield 1.0 mg (1% yield) of the title compound as a black solid. $^1$H NMR (200 MHz, d$^6$ DMSO) δ: 6.0 (brs, 6H), 6.92 (d, 1H), 7.18 (d, 1H), 7.38 (s, 1H), 10.60 (brs, 1H).

Example 30

Synthesis of 3,5-Diamino-4-[(4-methylsulfanylphenyl)hydrazono]pyrazole

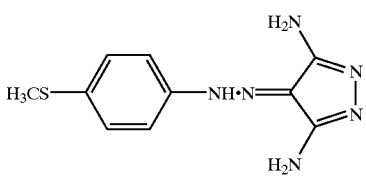

This compound was prepared using 108 mg (0.5 mmol) of 2-[(4-methylsulfanylphenyl)-hydrazono]malononitrile, which was derived from 4-methylthioaniline (117 mg, 1.0 mmol) and malononitrile (1.5 mmol) as described in Example 8, and hydrazine hydrate. Precipitate formed in the reaction tube immediately after the addition of hydrazine hydrate. The resulting solid was isolated by filtration, washed with ethanol, and dried to yield 95 mg (77%) of the title compound as an orange solid.

Example 31

Synthesis of 3,5-Diamino-4-[(2,3-dihydrobenzol[1,4]dioxin-6-yl)-hydrazono]pyrazole

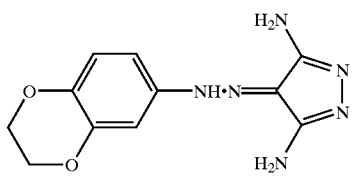

This compound was prepared using 114 mg (0.5 mmol) of 2-[(2,3-dihydro-benzo[1,4]dioxin-6-yl)hydrazono] malononitrile, which was derived from 1,4-benzodiozan-6-amine (151 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared. Very little solid had formed after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 35 mg (27%) of the title compound as a tan coloured solid.

Example 32

Synthesis of 3,5-Diamino-4-[(3-chloro-4-methoxyphenyl)hydrazono]pyrazole

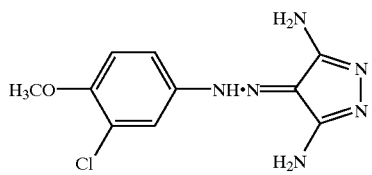

This compound was prepared using 117 mg (0.5 mmol) of 2-[(3-chloro-4-methoxy-phenyl)hydrazono]malononitrile, which was derived from 3-chloro-4-anisidine (157 mg, 1.0 mmol) and malononitrile (1.5 mmol) as described in Example 8, and hydrazine hydrate. Precipitate formed in the reaction tube immediately after the addition of hydrazine hydrate. The resulting solid was isolated by filtration, washed with ethanol, and dried to yield 93 mg (70%) of the title compound as a yellow solid.

Example 33

Synthesis of 3,5-Diamino-4-[(3,4-dichlorophenyl) hydrazono]pyrazole

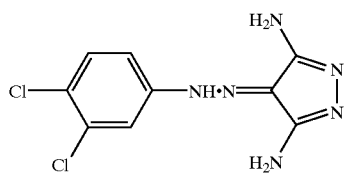

This compound was prepared using 120 mg (0.5 mmol) of 2-[(3,4-dichlorophenyl)-hydrazono]malononitrile, which was derived from 3,4-dichloroaniline (162 mg, 1.0 mmol) and malononitrile (1.5 mmol) as described in Example 8, and hydrazine hydrate. Precipitate formed in the reaction tube immediately after the addition of hydrazine hydrate. The resulting solid was isolated by filtration, precipitated from an ethyl acetate solution by the addition of hexanes, and dried to yield 53 mg (39%) of the title compound as a yellow solid. $^1$H NMR (ppm, DMSO-d$_6$): 6.30 (br, s, 4H), 7.55–7.79 (m, 2H), 7.95 (s, 1H), 10.80 (s, 1H).

Example 34

Synthesis of 3,5-Diamino-4-[(3,5-dichlorophenyl) hydrazono]pyrazole

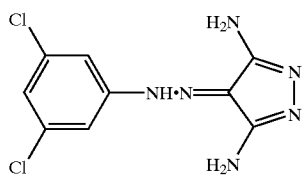

This compound was prepared using 120 mg (0.5 mmol) of 2-[(3,5-dichlorophenyl)-hydrazonolmalononitrile, which was derived from 3,5-dichloroaniline (162 mg, 1.0 mmol) and malononitrile (1.5 mmol) as described in Example 8, and hydrazine hydrate. Precipitate formed in the reaction tube approximately 5 min after the addition of hydrazine hydrate. The resulting solid was isolated by filtration, precipitated from an ethyl acetate solution by the addition of hexanes, and dried to yield 25 mg (18%) of the title compound as a yellow solid.

Example 35

Synthesis of 3,5-Diamino-4-[(2-isopropylphenyl)hydrazono]pyrazole

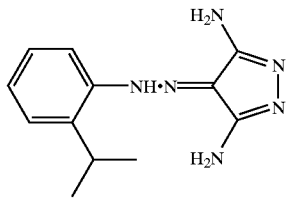

This compound was prepared using 106 mg (0.5 mmol) of 2-[(2-isopropylphenyl)-hydrazono]malononitrile, which was derived from 2-isopropylaniline (142 μL, 1.0 mmol) and malononitrile (1.5 mmol) as described in Example 8, and hydrazine hydrate. Precipitate formed in the reaction tube approximately 5 min after the addition of hydrazine hydrate. The resulting solid was isolated by filtration, washed with ethanol, and dried to yield 90 mg (73%) of the title compound as a greenish yellow solid.

Example 36

Synthesis of 3,5-Diamino-4-[(3,4-demithoxyphenyl)hydrazono]pyrazole

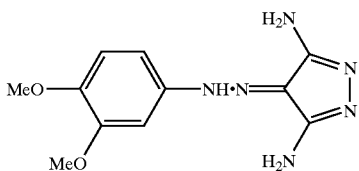

This compound was prepared using 115 mg (0.5 mmol) of 2-[(3,4-dimethoxyphenyl)-hydrazono]malononitrile, which was derived from 4-aminoveratrole (153 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared. Very little solid had formed after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 46 mg (35%) of the title compound as a mustard coloured solid.

Example 37

Synthesis of 3,5-Diamino-4-[(3-trifluoromethylphenyl)hydrazono]pyrazole

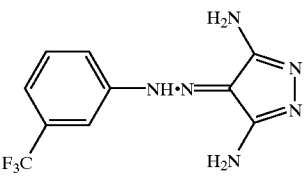

This compound was prepared using 119 mg (0.5 mmol) of 2-[(3-trifluoromethylphenyl)-hydrazono]malononitrile, which was derived from 3-(trifluoromethyl)aniline (125 μL, 1.0 mmol) and malononitrile (1.5 mmol) as described in Example 8, and hydrazine hydrate. Precipitate formed in the reaction tube approximately 10 min after the addition of hydrazine hydrate. The resulting solid was isolated by filtration, washed with ethanol, and dried to yield 43 mg (31%) of the title compound as a yellow solid.

Example 38

Synthesis of 3-N'-(3,5-Diaminopyrazol-4-ylidene)hydrazino]benzoic Acid Ethyl Ester

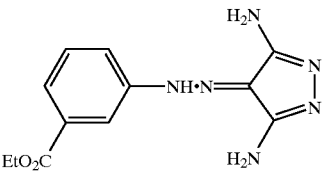

The title compound was prepared using 121 mg (0.5 mmol) of 3-(N'-dicyanomethylene-hydrazino)benzoic acid ethyl ester, which was derived from 3-aminobenzoate (149 μL, 1.0 mmol) and malononitrile (1.5 mmol) as described in Example 8, and hydrazine hydrate. Precipitate formed in the reaction tube approximately 10 min after the addition of hydrazine hydrate. The resulting solid was isolated by filtration, washed with ethanol, and dried to yield 58 mg (42%) of the title compound as a light brown solid.

Example 39

Synthesis of 3,5-Diamino-4-[(3-methoxy-5-trifluoromethylphenyl)-hydrazono]pyrazole

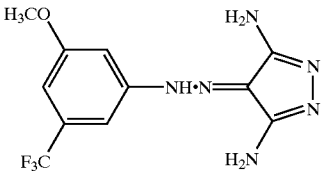

This compound was prepared using 134 mg (0.5 mmol) of 2-[(3-methoxy-5-trifluoromethylphenyl)hydrazono]malononitrile, which was derived from 3-methoxy-5-trifluoromethylaniline (191 mg, 1.0 mmol) and malononitrile (1.5 mmol) as described in Example 8, and hydrazine hydrate. Very little solid had formed after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 10 mg (7%) of the title compound as a yellow solid.

Example 40

Synthesis of 3,5-Diamino-4-[(2-chlorophenyl) hydrazono]pyrazole

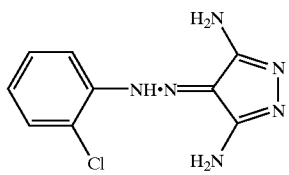

This compound was prepared using 102 mg (0.5 mmol) of 2-[(2-chlorophenyl)-hydrazono]malononitrile, which was derived from 2-chloroaniline (105 μL, 1.0 mmol) and malononitrile (1.5 mmol) as described in Example 8, and hydrazine hydrate. Precipitate formed in the reaction tube approximately 10 min after the addition of hydrazine hydrate. The resulting solid was isolated by filtration, washed with ethanol, and dried to yield 34 mg (29%) of the title compound as a yellow solid.

Example 41

Synthesis of 3,5-Diamino-4-[(3-iodophenyl) hydrazono]pyrazole

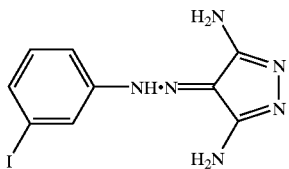

This compound was prepared using 148 mg (0.5 mmol) of 2-[(3-iodophenyl)hydrazono]-malononitrile, which was derived from 3-iodoaniline (219 mg, 1.0 mmol) and malononitrile (1.5 mmol) as described in Example 8, and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 122 mg (74%) of the title compound as a mustard coloured solid.

Example 42

Synthesis of 3,5-Diamino-4-[(9-ethyl-9-carbazol-3-yl)hydrazono]pyrazole

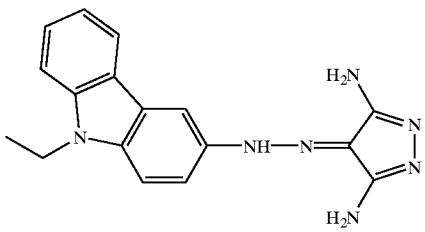

This compound was prepared using 143 mg (0.5 mmol) of 2-[(9-ethyl-9H-carbazol-3-yl)-hydrazono]malononitrile, which was derived from 3-amino-9-ethylcarbazole (210 mg, 1.0 mmol) and malononitrile (1.5 mmol) as described in Example 8, and hydrazine hydrate. Solids had not formed after heating the reaction at 75° C. for 1 hr, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 46 mg (29%) of the title compound as a black solid.

Example 43

Synthesis of 3,5-Diamino-4-[(2-benzenesulfonylphenyl)hydrazono]pyrazole

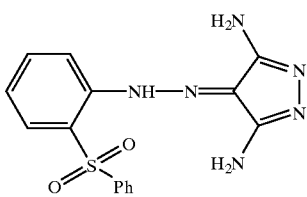

This compound was prepared using 94 mg (0.5 mmol) of 2-[(2-benzenesulfonylphenyl)-hydrazono]malononitrile, which was derived from 2-(phenylsulfonyl)aniline (233 mg, 1.0 mmol) and malononitrile (1.5 mmol) as described in Example 8, and hydrazine hydrate. Precipitate formed in the reaction tube approximately 20 min after the addition of hydrazine hydrate. The resulting solid was isolated by filtration, washed with ethanol, and dried to yield 68 mg (20%) of the title compound as an orange coloured solid.

Example 44

Synthesis of 3,5-Diamino-1-phenyl-4-phenylazopyrazole

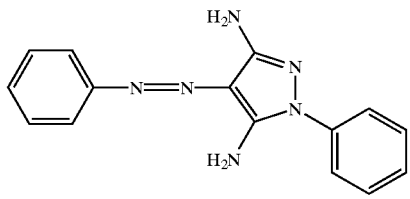

This compound was prepared using 200 mg (1.2 mmol) of 2-(phenylhydrazono)-malononitrile, which was derived from aniline (10 mL, 107 mmol) and malononitrile (161 mmol) as described in Example 8, and phenylhydrazine (767 mg, 7.1 mmol). Solids had not formed after heating the reaction at 75° C. for 3 hrs, however, analysis of the reaction solution by TLC indicated that no starting material remained. The solution was allowed to cool to room temperature and the solvent was evaporated. The residue was dissolved in ethyl acetate and then precipitated by the addition of hexanes. The resulting solid was isolated by filtration and dried to yield 77 mg (23%) of the title compound as an orange coloured solid.

Example 45

Synthesis of (3,5-Diamino-4-phenylazo-pyrazol-1-yl)phenylmethanone

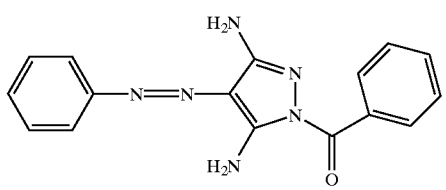

This compound was prepared using 85 mg (0.5 mmol) of 2-(phenyl-hydrazono)-malononitrile, which was derived from aniline (10 mL, 107 mmol) and malononitrile (161 mmol) as described in Example 8, and benzoic hydrazide (68 mg, 0.5 mmol). Solids had not formed after heating the reaction at 75° C. for 3 hrs, however, analysis of the reaction solution by TLC indicated that no starting material remained. The solution was allowed to cool to room temperature and the solvent was evaporated. The residue was dissolved in methanol and then precipitated by the addition of water. The resulting solid was isolated by filtration and dried to yield 20 mg (13%) of the title compound as an orange coloured solid.

Example 46

Synthesis of 3,5-Diamino-1-(4-bromophenyl)-4-phenylazopyrazole

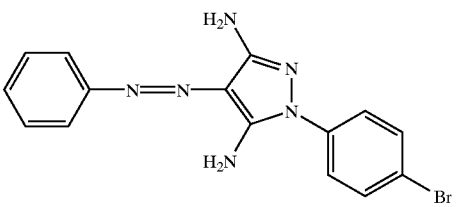

This compound was prepared using 85 mg (0.5 mmol) of 2-(phenylhydrazono) malononitrile, which was derived from aniline (10 mL, 107 mmol) and malononitrile (161 mmol) as described in Example 8, and 4-bromophenylhydrazine hydrochloride (112 mg, 0.5 mmol) with the addition of 0.5 mL of 5% sodium hydroxide solution. Solids had not formed after heating the reaction at 75° C. for 3 hrs, however, analysis of the reaction solution by TLC indicated that no starting material remained. The solution was allowed to cool to room temperature and the solvent was evaporated. The residue was dissolved in methanol and then precipitated by the addition of water. The resulting solid was isolated by filtration and dried to yield 49 mg (27%) of the title compound as a brown solid.

Example 47

Synthesis of (3,5-Diamino-4-phenylazopyrazol-1-yl)benzoic Acid

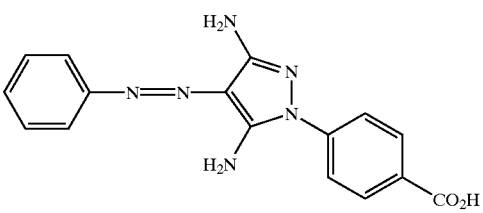

This compound was prepared using 85 mg (0.5 mmol) of 2-(phenylhydrazono)-malononitrile, which was derived from aniline (10 mL, 107 mmol) and malononitrile (161 mmol) as described in Example 8, and 4-hydrazinobenzoic acid (76 mg, 0.5 mmol). After reacting for 4 hrs, the reaction remained as a slurry; however, analysis of the reaction solution by TLC indicated that no starting material remained. The resulting solid was isolated by filtration, washed with ethanol, and dried to yield 22 mg (14%) of the title compound as a brown solid.

Example 48

Synthesis of 3,5-Diamino-1-(4-fluorophenyl)-4-phenylazopyrazole

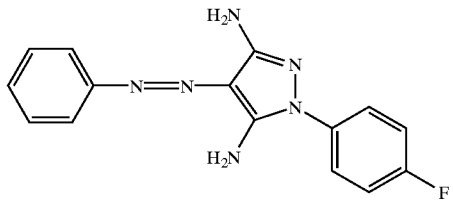

This compound was prepared using 85 mg (0.5 mmol) of 2-(phenylhydrazono)-malononitrile, which was derived from aniline (10 mL, 107 mmol) and malononitrile (161 mmol) as described in Example 8, and 4-fluorophenylhydrazine hydrochloride (81 mg, 0.5 mmol) with the addition of 0.5 mL of 5% sodium hydroxide solution. After reacting for 4 hrs, very little solid had formed; however, analysis of the reaction solution. by TLC indicated that no starting material remained. The resulting solid was removed by filtration and the solvent was evaporated from the filtrate to yield 29 mg (20%) of the title compound as a brown solid.

Example 49

Synthesis of 3,5-Diamino-4-[(pyridin-3-yl)hydrazono]pyrazole

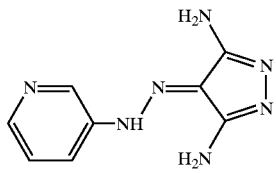

This compound was prepared using 2-[(pyridin-3-yl)hydrazono]malononitrile (342 mg, 2 mmole), which was derived from 3-aminopyridine (940 mg, 10 mmole)) and malononitrile (858 mg, 13 mmol) as described in Example 8, and hydrazine hydrate (110 mg, 2.2 mmole) in ethanol. Solids had not formed after heating the reaction at 80° C. for 40 minutes, however, analysis of the reaction solution by TLC indicated that no starting material remained. The solution was allowed to cool to room temperature and the solvent was evaporated. The product was obtained after upon re-crystallization from ethanol as a yellow solid (150 mg). $^1$H NMR (ppm, DMSO-$d_6$): 6.18 (br., s, 4H), 7.20 (dd, 1H), 8.00 (dd, 1H), 8.38 (d, 1H), 8.85 (s, 1H), 10.77 (br., s, 1H).

Example 50

Synthesis of 5-Amino-4-[(3-fluorophenyl)hydrazono]-2,4-dihydropyrazole-3-one

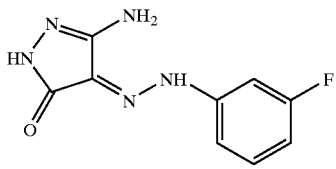

This compound was prepared using 2-[(3-fluorophenyl)hydrazono]malononitrile (145 mg, 0.5 mmole), which was derived from 3-fluoroaniline (111 mg, 1 mmole)) and cyclohexyl cyanoacetate (217 mg, 1.3 mmole) as described in Example 8, and hydrazine hydrate (25 mg, 0.5 mmole) in ethanol. Solids had not formed after heating the reaction at 80° C. for 40 minutes, however, analysis of the reaction solution by TLC indicated that no starting material remained. The solution was allowed to cool to room temperature and concentrated. The product was obtained after filtration as a yellow solid (73 mg). $^1$H NMR (ppm, DMSO-$d_6$): 5.95 (br., s, 2H), 6.90 (m, 1H), 7.20–7.65 (m, 3H), 10.56 (br., s, 1H) 12.77 (br., s, 1H).

Example 51

Synthesis of 3,5-Diamino-4-[(6-methoxybenzothiazol-2-yl)hydrazono]pyrazole

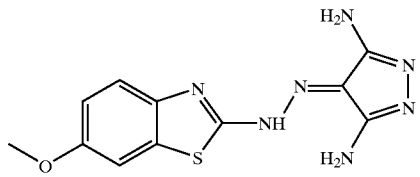

This compound was prepared using 2-[(6-methoxybenzothiazol-2-yl)hydrazono]-malononitrile (200 mg), which was derived from 2-amino-6-methoxybensothiazole (1.17 g) and malononitrile (0.82 g) as described in Example 8, and hydrazine hydrate (0.2 mL) in ethanol. Solids had not formed after heating the reaction at 40° C. for 2 hrs. The solution was allowed to cool to room temperature and concentrated. The product was obtained after column chromatography purification (80 mg, 35%).

Example 52

Synthesis of 3,5-Diamino-4-[(benzothiazol-2-yl)hydrazono]pyrazole

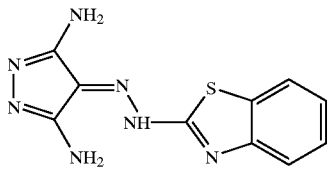

This compound was prepared using 2-[(6-benzothiazol-2-yl)hydrazono]malononitrile (80 mg), which was derived from 2-aminobensothiazole (925 mg) and malononitrile (0.65 g) as described in Example 8, and hydrazine hydrate (0.1 mL) in ethanol. Solids had not formed after heating the reaction at 60° C. for 3 hrs. The solution was allowed to cool to room temperature and concentrated. The product was obtained after thin layer chromatography purification (47 mg, 50%).

Example 53

Synthesis of 3,5-Diamino-4-[(pyrazol-3-yl) hydrazono]pyrazole

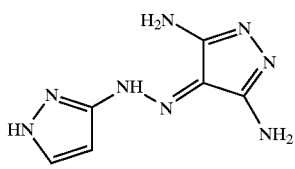

This compound was prepared using 3-aminopyrazole (0.5 g), malononitrile (1.8 g), and hydrazine hydrate (0.3 g) as described in Example 1. The product was obtained after column chromatography purification (157 mg, 14%).

Example 54

Synthesis of 3,5-Diamino-4-[(pyridin-4-yl) hydrazono]pyrazole

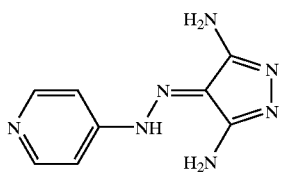

4-Aminopyridine (0.36 g) was dissolved in a mixture of 2 ml of $H_3PO_4$ (85%) and 1 ml of $HNO_3$ (68%). The solution was cooled at −5° C. and then $NaNO_2$ (0.28 g) solution was added. After being stirred at 0° C. for 1 hr., the mixture was added dropwise into a solution of malononitrile (0.5 g), acetic acid (2.4 g), KOAc (6.3 g) and $Na_2CO_3$ (5.6 g). The resulting mixture was kept stirring at 0° C. for 1 hr, and 100 mL of water was added. The solid obtained after being filtered and dried was re-dissolved in 5 mL of EtOH and hydrazine hydrate (0.5 g) was added at 40° C. After one hour of reaction, the solid precipitated upon cooling to 0° C. was collected by filtration and the pure product was obtained after re-crystallization from EtOH (278, mg, 36%).

Example 55

Synthesis of 3,5-Diamino-4-[(2,3,4,5,6-pentafluorophenyl)hydrazono]pyrazole

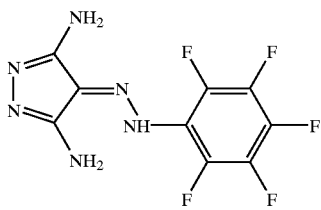

Pentafluoroaniline (1.0 g) dissolved in 12 mL of $CH_3COOH$ was added into a solution of $NaNO_2$ (0.41 g) in concentrated $H_2SO_4$ at 5° C. The reaction mixture was kept stirring at 5° C. for 1 hr and then slowly added into a solution of malononitrile (1.0 g) mixed with 37 g of NaOAc in 50 mL of $H_2O$ at 5–10° C. The reaction mixture was extracted with EtOAc (3×150 mL) ah hour later. The combined organic phase was washed with brine, dried with anhydrous $MgSO_4$ and then evaporated. The residue was dissolved in 5 ml of anhydrous EtOH and 0.2 g of $N_2H_4$ was added to it at 40° C. After being stirred at 70° C. for 2 hrs., the solvents were removed and the residue was purified by column yielding 87 mg of the product (5.4%).

Example 56

Synthesis of 3,5-Diamino-4-[(31,2,4-triazolo) hydrazono]pyrazole

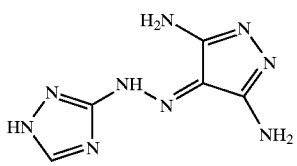

This compound was prepared using the same method as described in Example 1. 3-Amino-1,2,4-triazole (0.88 g), malononitrile (1.0 g), and hydrazine hydrate (0.5 ml) yielded 34 mg of the product (6%).

Example 57

Synthesis of 3,5-Diamino-4-[(3,5-difluorophenyl) hydrazono]pyrazole

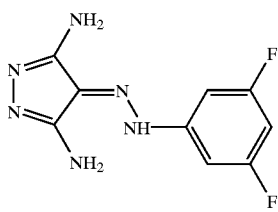

This compound was prepared using the same method as described in Example 1. 3,5-Difluoroaniline (0.31 g), malononitrile (0.4 g) and hydrazine hydtrate (0.2 g) yielded 0.201 g of the product (35%).

Example 58

Synthesis of 3,5-Diamino-4-[(2,3,4-trifluorophenyl) hydrazono]pyrazole

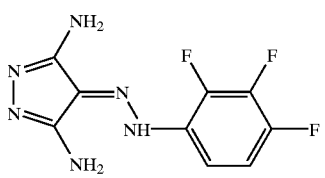

This compound was prepared using the method as described in Example 1. 2,3,4-Trifluoroaniline (0.36 g), malononitrile (0.4 g) and hydrazine hydrate (0.2 g) yielded 0.337 g of the product (54%).

Example 59

Synthesis of 3,5-Diamino-1-methyl-4-phenylazopyrazole

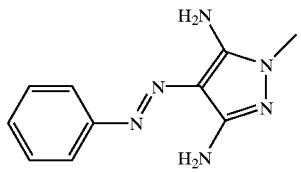

This compound was prepared using the method as described in Example 1 using 2-phenylhydrazonomalononitrile (425 mg) and methylhydrazine sulfate (720 mg). The product was purified by column chromatography and afforded a yellow solid.

What is claimed is:

1. A composition comprising a compound of formula (1)

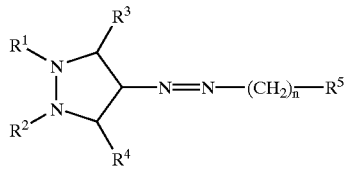

(1)

or a stereoisomer, polymorph, solvate, or a pharmaceutically acceptable salt thereof, and a pharmaceutically acceptable carrier, diluent or excipient, where $R^1$ is selected from alkyl, aryl and heteroaryl, wherein each of alkyl, aryl and heteroaryl may be substituted with one or more groups selected from $C_1$–$C_{20}$alkyl, $C_6$–$C_{10}$aryl, heteroalkyl and heteroaryl;

$R^2$ is selected from H and direct bond;

$R^3$ and $R^4$ are selected from —$NH_2$ and NHC(=O)$R^5$;

$R^5$ is selected from $R^6$, $R^7$, and $R^8$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; $R^8$ is selected from $(R^7)_k$-alkylene, $(R^7)_k$-heteroalkylene, $(R^7)_k$-arylene, and $(R^7)_k$-heteroarylene; and k is selected from 0, 1, 2, 3, 4 and 5; and n is selected from 0, 1, 2, 3, 4 or 5.

2. The composition of claim 1 wherein $R^1$ is $C_1$–$C_{20}$alkyl.

3. The composition of claim 2 wherein $R^1$ is $C_1$–$C_6$alkyl and each of $R^3$ and $R^4$ are —$NH_2$.

4. The composition of claim 1 wherein $R^1$ is aryl.

5. The composition of claim 4 wherein $R^1$ is aryl selected from phenyl and naphthyl, the phenyl and napthyl substituted with at least one heteroalkyl selected from alkoxy, carboxy and halide.

6. The composition of claim 5 wherein each of $R^3$ and $R^4$ are —$NH_2$.

7. The composition of claim 1 wherein $R^5$ is selected from carbocyclic and heterocyclic groups.

8. The composition of claim 7 wherein the carbocyclic and heterocyclic groups contain 5–12 ring atoms.

9. The composition of claim 1 wherein $R^5$ is a carbocyclic group selected from monocyclic and fused ring groups.

10. The composition of claim 1 wherein $R^5$ is a heterocyclic group containing from 1–3 heteroatoms selected from nitrogen and sulfur.

11. The composition of claim 1 wherein $R^5$ is selected from $R^6$ and $R^7$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; and k is selected from 0, 1, 2, 3, 4 and 5.

12. The composition of claim 1 wherein $R^5$ is selected from 4-fluorophenyl, 3-ethylphenyl, 3-methoxyphenyl, 3-chlorophenyl, 3-fluorophenyl, 3-fluoro-4-methoxyphenyl, naphthalen-2-yl, 4-trifluoromethylphenyl, 3-phenoxyphenyl, biphenyl-2-yl, 2-bromophenyl, 3-bromophenyl, 4-bromophenyl, 4-phenoxyphenyl, 4-iodophenyl, 4-bromonaphthalen-1-yl, o-tolyl, 2,6-difluorophenyl, 3,4-difluorophenyl, benzo[1,3]dioxol-5-yl, 4-methylsulfanylphenyl, 2,3-dihydrobenzo[1,4]dioxin-6-yl, 3-chloro-4-methoxyphenyl, 3,4-dichlorophenyl, 3,5-dichlorophenyl, 2-isopropylphenyl, 3,4-dimethoxyphenyl, 3-trifluoromethylphenyl, 3-methoxy-5-trifluoromethylphenyl, 2-chlorophenyl, 3-iodophenyl, 9-ethyl-9H-carbazol-3-yl, 2-benzenesulfonylphenyl, phenyl, pyridin-3-yl, 6-methoxybenzothiazol-2-yl, benzothiazol-2-yl, pyrazol-3-yl, pyridin-4-yl, 2,3,4,5,6-pentafluorophenyl, 3-[1H]-1,2,4-triazolo, 3,5-difluorophenyl, and 2,3,4-trifluorophenyl.

13. The composition of claim 12 wherein each of $R^3$ and $R^4$ are —$NH_2$.

14. The composition of claim 13 wherein $R^1$ is $C_1$–$C_{20}$alkyl.

15. The composition of claim 13 wherein $R^1$ is aryl.

16. The composition of claim 13 wherein $R^1$ is heteroaryl.

17. The composition of claim 1 wherein the compound of formula (1) is selected from (3,5-diamino-4-phenylazo-pyrazol-1-yl) phenylmethanone;

4-(3,5-diamino-4-phenylazopyrazol-1-yl)benzoic acid;

3,5-diamino-1-phenyl-4-phenylazopyrazole;

3,5-diamino-1-(4-bromophenyl)4-phenylazopyrazole;

3,5-diamino-1-(4-fluorophenyl)4-phenylazopyrazole; and 3,5-diamino-1-methyl4-phenylazopyrazole.

18. A composition comprising a compound of formula (2)

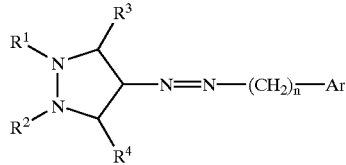

(2)

or a stereoisomer, polymorph, solvate, or a pharmaceutically acceptable salt thereof, and a pharmaceutically acceptable carrier, diluent or excipient, where $R^1$ and $R^2$ are selected from H and direct bond;

$R^3$ and $R^4$ are selected from —$NH_2$, NHC(=O)$R^5$ and =O; and

Ar is an aryl group.

19. A composition of claim 18 wherein Ar is phenyl having one or more substituents selected from alkyl, aryl, heteroalkyl and heteroaryl.

20. A composition of claim 19 wherein the substituents are selected from benzenesulfonyl, bromide, carbonylethoxy, carbonylmethoxy, chloride, dioxolyl, dioxinyl, ethyl, fluoride, hydroxyl, iodide, iso-propyl, methoxy, methyl, methylthio, phenoxy, phenyl, propyl, and trifluoromethyl.

21. A composition of claim 20 wherein the compound is selected from 3,5-diamino-4-[(4-fluorophenyl)hydrazono]pyrazole;
3-[N'-(3,5-diaminopyrazol-4-ylidene)hydrazino]phenol;
3,5-diamino-4-[(3-ethylphenyl)hydrazono]pyrazole;
3,5-diamino-4-[(3-methoxyphenyl)hydrazono]pyrazole;
3,5-diamino-4-[(3-chlorophenyl)hydrazono]pyrazole;
3,5-diamino-4-[(3-fluorophenyl)hydrazono]pyrazole;
3,5-diamino-4-[(3-fluoro-4-methoxyphenyl)hydrazono]pyrazole;
3,5-diamino-4-[(4-trifluoromethylphenyl)hydrazono]pyrazole;
4-[(3-phenoxyphenyl)hydrazono]pyrazole;
4-[N'-(3,5-diaminopyrazol-4-ylidene)hydrazino]benzoic acid ethyl ester;
3,5-diamino-4-[(biphenyl-2-yl)hydrazono]pyrazole;
3,5-diamino-4-[(2-bromophenyl)hydrazono]pyrazole;
3,5-diamino-4-[(3-bromophenyl)hydrazono]pyrazole;
3,5-diamino-4-[(4-bromophenyl)hydrazono]pyrazole;
3,5-diamino-4-[(4-phenoxyphenyl)hydrazono]pyrazole;
3,5-diamino-4-[(4-iodophenyl)hydrazono]pyrazole;
3,5-diamino-4-[(o-tolyl)hydrazono]pyrazole
3,5-diamino-4-[(2,6-difluorophenyl)hydrazono]pyrazole;
3,5-diamino-4-[(3,4-difluorophenyl)hydrazono]pyrazole;
3,5-diamino-4-[(benzo[1,3]dioxol-5-yl)hydrazono]pyrazole;
3,5-diamino-4-[(4-methylsulfanylphenyl)hydrazono]pyrazole;
3,5-diamino-4-[(2,3-dihydrobenzo[1,4]dioxin-6-yl)-hydrazono]pyrazole;
3,5-diamino-4-[(3-chloro-4-methoxyphenyl)hydrazono]pyrazole;
3,5-diamino-4-[(3,4-dichloro phenyl)hydrazono]pyrazole;
3,5-diamino-4-[(3,5-dichlorophenyl)hydrazono]pyrazole;
3,5-diamino-4-[(2-isopropylphenyl)hydrazono]pyrazole;
3,5-diamino-4-[(3,4-dimethoxyphenyl)hydrazono]pyrazole;
3,5-diamino-4-[(3-trifluoromethylphenyl)hydrazono]pyrazole;
3-[N'-(3,5-diaminopyrazol-4-ylidene)hydrazino]benzoic acid ethyl ester;
3,5-diamino-4-[(3-methoxy-5-trifluoromethylphenyl)-hydrazono]pyrazole;
3,5-diamino-4-[(2-chlorophenyl)hydrazono]pyrazole;
3,5-diamino-4-[(3-iodophenyl)hydrazono]pyrazole; and
3,5-diamino-4-[(2-benzenesulfonylphenyl)hydrazono]pyrazole.

22. A composition of claim 18 wherein Ar is naphthyl optionally having one or more substituents selected from alkyl, aryl, heteroalkyl and heteroaryl.

23. A composition of claim 22 wherein the substituents are selected from benzenesulfonyl, bromide, carbonylethoxy, carbonylmethoxy, chloride, dioxolyl, dioxinyl, ethyl, fluoride, hydroxyl, iodide, iso-propyl, methoxy, methyl, methylthio, phenoxy, phenyl, propyl, and trifluoromethyl.

24. A composition of claim 23 wherein the compound is selected from
3,5-diamino-4-[(naphthalen-2-yl)hydrazono]pyrazole; and
3,5-diamino-4-[(4-bromonaphthalen-1-yl)hydrazono]pyrazole.

25. A composition comprising a compound of formula (1)

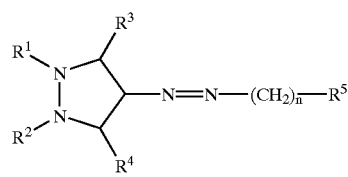

(1)

or a stereoisomer, solvate, polymorph, or a pharmaceutically acceptable salt thereof, and a pharmaceutically acceptable carrier, diluent or excipient, where
$R^1$ and $R^2$ are selected from H and direct bond;
$R^3$ and $R^4$ are selected from —$NH_2$ and NHC(=O)$R^5$;
$R^5$ is selected from heteroaryl and substituted heteroaryl, where a substituent on substituted heteroaryl is selected from alkyl, heteroalkyl, aryl and heteroaryl.

26. A composition according to claim 25 wherein the compound is selected from:
3,5-diamino-4-[(9-ethyl-9H-carbazol-3-yl)hydrazono]pyrazole;
3,5-diamino-4-[(pyridin-3-yl)hydrazono]pyrazole;
3,5-diamino-4-[(6-methoxybenzothiazol-2-yl)hydrazono]pyrazole; and
3,5-diamino-4-[(benzothiazol-2-yl )hydrazono]pyrazole.

* * * * *